(12) United States Patent
Wallace et al.

(10) Patent No.: US 12,377,181 B2
(45) Date of Patent: Aug. 5, 2025

(54) STERILIZATION SYSTEM AND METHOD

(71) Applicants: David Wallace, Mesa, AZ (US); John Patterson, Tempe, AZ (US); Nikhil Dave, Chandler, AZ (US); Abhik Chowdhury, Chandler, AZ (US); Katie Sue Pascavis, Gilbert, AZ (US)

(72) Inventors: David Wallace, Mesa, AZ (US); John Patterson, Tempe, AZ (US); Nikhil Dave, Chandler, AZ (US); Abhik Chowdhury, Chandler, AZ (US); Katie Sue Pascavis, Gilbert, AZ (US)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 449 days.

(21) Appl. No.: 17/243,328

(22) Filed: Apr. 28, 2021

(65) Prior Publication Data

US 2021/0338871 A1   Nov. 4, 2021

Related U.S. Application Data

(60) Provisional application No. 63/018,389, filed on Apr. 30, 2020.

(51) Int. Cl.
*A61L 2/20* (2006.01)
*A61L 2/24* (2006.01)
*A61L 2/26* (2006.01)

(52) U.S. Cl.
CPC ............... *A61L 2/208* (2013.01); *A61L 2/24* (2013.01); *A61L 2/26* (2013.01); *A61L 2202/11* (2013.01);

(Continued)

(58) Field of Classification Search
CPC ... A61L 2/208; A61L 2/24; A61L 2/26; A61L 2202/11; A61L 2202/122; A61L 2202/14; A61L 2202/15
See application file for complete search history.

(56) References Cited

U.S. PATENT DOCUMENTS 5,792,422 A * 8/1998 Lin ..................... A61L 2/186
422/29
6,248,136 B1 * 6/2001 McClain .............. D06L 1/02
8/142

(Continued)

FOREIGN PATENT DOCUMENTS

WO   WO-2020049224 A1 *  3/2020  ............... A61L 2/04

OTHER PUBLICATIONS

Arizona State University, "COVID-19 Rapid Response Sterilization Procedure for Nasal Swab Extenders," Luminosity Lab, dated Mar. 29, 2020.

(Continued)

*Primary Examiner* — Regina M Yoo
(74) *Attorney, Agent, or Firm* — Michael Best & Friedrich LLP

(57) ABSTRACT

A sterilization system includes a vessel defining a chamber configured to receive one or more materials, a hydrogen peroxide solution positioned within the chamber, and a nonreactive fiber matrix positioned within the chamber, wherein evacuation of the chamber causes vaporization of the hydrogen peroxide in the hydrogen peroxide solution to disinfect the materials positioned in the chamber.

15 Claims, 16 Drawing Sheets

(52) U.S. Cl.
CPC ....... *A61L 2202/14* (2013.01); *A61L 2202/15* (2013.01); *A61L 2202/24* (2013.01)

(56) References Cited

U.S. PATENT DOCUMENTS

| | | | |
|---|---|---|---|
| 6,451,272 B1* | 9/2002 | Fryer | G01N 31/223 |
| | | | 436/1 |
| 7,850,931 B2 | 12/2010 | McDonnell et al. | |
| 8,685,329 B2 | 4/2014 | Lee | |
| 9,364,571 B2* | 6/2016 | Ahiska | A61L 2/208 |
| 2002/0022246 A1* | 2/2002 | Lin | A61L 2/24 |
| | | | 436/1 |
| 2011/0176959 A1 | 7/2011 | Ko | |
| 2017/0175069 A1* | 6/2017 | Baker, Jr. | C12M 37/06 |
| 2017/0304477 A1* | 10/2017 | Truong | G01N 33/18 |
| 2018/0252466 A1* | 9/2018 | Baker | B01L 7/52 |
| 2020/0069826 A1* | 3/2020 | Lim | A61L 2/22 |
| 2021/0330843 A1* | 10/2021 | Hakkarainen | B01D 1/14 |
| 2021/0386890 A1* | 12/2021 | Hakkarainen | A61L 2/208 |
| 2022/0111093 A1* | 4/2022 | Storey | A61L 2/208 |
| 2022/0226528 A1* | 7/2022 | Fryer | G01N 31/226 |

OTHER PUBLICATIONS

ISM and IS Med Specialties, "Plastics and Compatibility with Sterilization Methods," <https://www.industrialspec.com/resources/plastics-sterilization-compatibility?utm_source=plas-sterilize&utm_medium=pdf> dated Jan. 23, 2019.

Li et al., "Surface Germicidal Effects of Ozone for Microorganisms," AIHA Journal, (2003), 64:533-537.

Oth et al., "How to Sterilize 3D Printed Objects for Surgical Use? An Evaluation of the Volumetric Deformation of 3D-Printed Genioplasty Guide in PLA and PETG after Sterilization by Low-Temperature Hydrogen Peroxide Gas Plasma," The Open Dentistry Journal, 2019, vol. 13, 410-417.

Sosnowski et al., "Sterilization of Medical 3D Printed Plastics: Is H2O2 Vapour Suitable?," 2017 CMBEC40 Conference, Winnipeg MB, May 23-26, 2017.

* cited by examiner

Max 4 Per Layer

STERILIZATION SYSTEM AND METHOD

CROSS-REFERENCE TO RELATED APPLICATIONS

This application is a non-provisional of and claims the benefit of U.S. Patent Application No. 63/018,389, filed on Apr. 30, 2020, the contents of which are incorporated herein by reference.

FIELD

The present disclosure relates to a sterilization system and method. In particular, the present disclosure relates to a sterilization system and method that uses hydrogen peroxide.

BACKGROUND

The COVID-19 outbreak has resulted in an unprecedented strain on the global personal protective equipment (PPE) supply chain. Particularly, the demand for face coverings such as surgical masks and medical-grade N95 respirators (i.e., N95 masks) has increased substantially throughout the COVID-19 pandemic in order to prevent the spread of SARS-CoV-2. In turn, medical professionals and community members have turned to alternative mechanisms for sterilizing and reusing their existing stockpile of face coverings and N95 respirators.

SUMMARY

The present disclosure is a process chamber employing vaporized hydrogen peroxide as a disinfecting agent for use in industrial, medical, consumer, or other applications. The disclosure describes a source of vaporized hydrogen peroxide that provides for disinfection purposes in a compact and easily manufacturable and deployable format.

The present disclosure pertains to any suitable use case where there is a need to disinfect materials using vaporized hydrogen peroxide, particularly in a use case where a compact and modular treatment chamber is required. In particular, vaporized hydrogen peroxide may be used for the disinfection and sterilization of medical supplies or personal protective equipment such as masks or re-usable medical equipment.

The present disclosure pertains to the use of a nonreactive fiber matrix, such as woven fiberglass, nonwoven fiberglass, mineral wool, etc. to accelerate the rate of evaporation of a hydrogen peroxide solution within an evacuated chamber. The use of this nonreactive fiber matrix to dispense hydrogen peroxide vapor without reacting with the hydrogen peroxide allows small evacuated vessels to be employed as disinfection chambers for the applications described above.

In one construction, a sterilization system includes a vessel defining a chamber configured to receive one or more materials, a hydrogen peroxide solution positioned within the chamber, and a nonreactive fiber matrix positioned within the chamber, wherein evacuation of the chamber causes vaporization of the hydrogen peroxide in the hydrogen peroxide solution to disinfect the materials positioned in the chamber.

In one construction, a method of sterilizing one or more materials includes positioning the one or more materials within a sterilization chamber of a vessel, combining hydrogen peroxide solution with a non-reactive fiber matrix within the vessel, and vaporizing the hydrogen peroxide in the hydrogen peroxide solution to sterilize the one or more materials within the sterilization chamber.

In one construction, a sterilization system includes a vessel defining a chamber configured to receive one or more materials, a hydrogen peroxide solution positioned within the chamber, a non-reactive fiber matrix positioned within the chamber, and a support assembly positioned within the chamber. The support assembly is configured to support the one or more materials. A vacuum source is in fluid communication with the chamber. The vacuum source is configured to evacuate the chamber. Evacuation of the chamber causes vaporization of the hydrogen peroxide in the hydrogen peroxide solution to disinfect the materials positioned in the chamber.

Other aspects of the invention will become apparent by consideration of the detailed description and accompanying drawings.

DETAILED DESCRIPTION

Before any constructions of the invention are explained in detail, it is to be understood that the invention is not limited in its application to the details of construction and the arrangement of components set forth in the following description or illustrated in the following drawings. The invention is capable of other constructions and of being practiced or of being carried out in various ways.

Recent literature highlights the efficacy of large-scale vaporized hydrogen peroxide (VHP) systems to sterilize N95 masks for reuse. The Food and Drug Administration (FDA) has reported achieving sterilization of N95 respirators using a Battelle VHP system, as indicated by 6-$\log_{10}$ reduction of bacteria, without affecting the filtration efficiency. The N95 fit was unaffected after 20 treatment cycles and the elastic did not degrade within 30 treatment cycles. Additionally, Duke University validated that proper sterilization was achieved, while Yale University and University of Manitoba, Winnipeg Canada demonstrated eradication of SARS-Cov-2 and other viruses acting as proxies. Further, sterilization of disposable N95 masks using VHP has been approved in some cases by both the FDA and the CDC, citing its biocidal activity against various biological particles including bacteria, severe acute respiratory syndrome coronavirus 2 (SARS-CoV-2), and other viruses.

However, these systems, including the Bioquell BQ-50 device and similar machines, are high in cost and require significant specialized labor to install, making it difficult to scale this model to the needs of individual community members. Given the increasing importance of PPE both in health care facilities as well as in various communities as they reopen in the coming months, there is a need for a cost-effective and scalable device that can sterilize any type of face covering, including N95 respirators.

Figure 1:
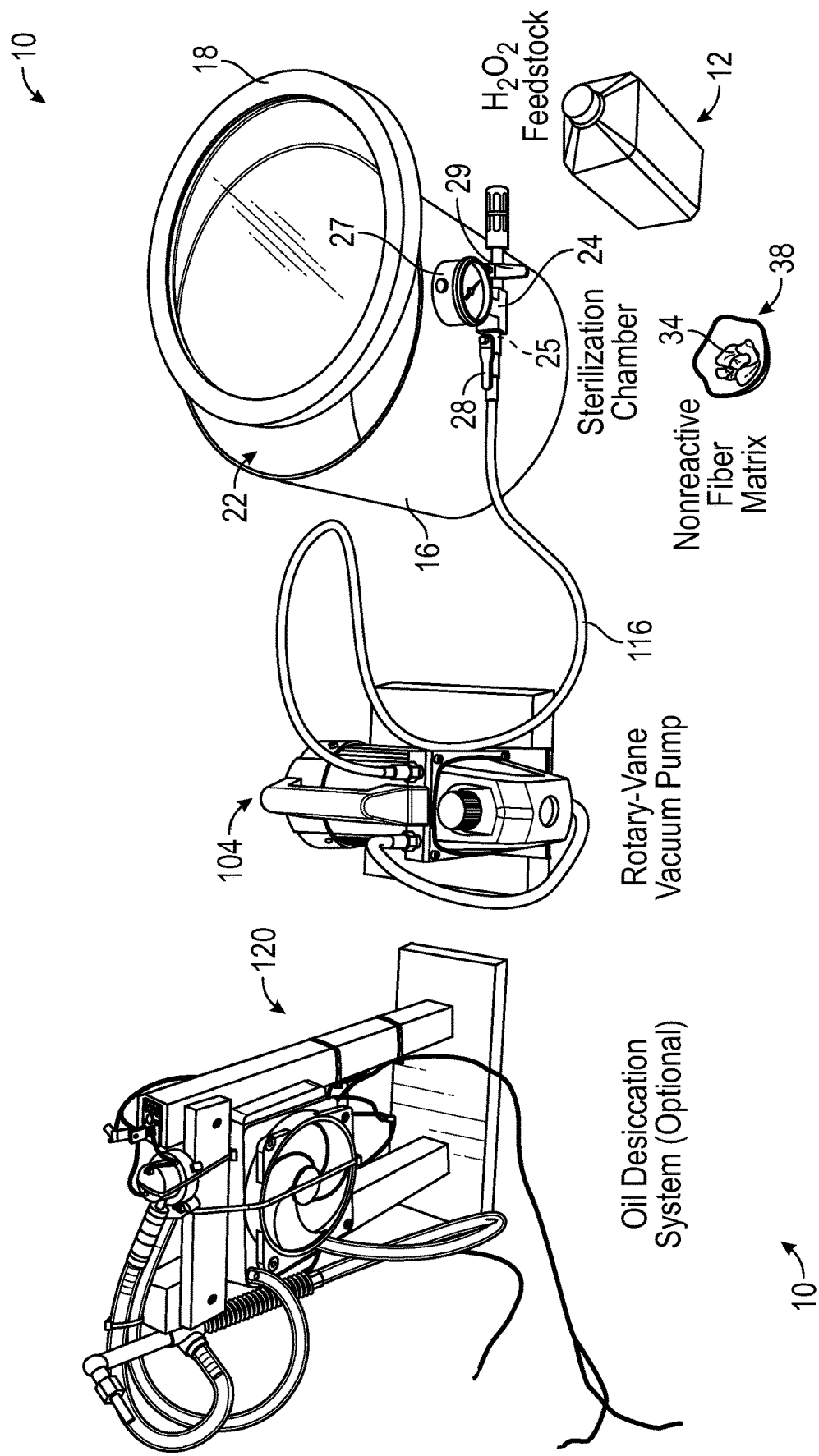
FIG. 1 is a detailed view of a sterilization system according to one construction and including a vessel having a sterilization chamber and a manifold.

FIG. 1 illustrates a sterilization system 10 (e.g., compact low-pressure vaporized hydrogen peroxide system) that vaporizes a hydrogen peroxide solution 12. The system 10 includes a container or vessel 14, a vacuum source 104, a heat source (not shown in FIG. 1), a dispenser (not shown in FIG. 1), and a conduit 116. In some constructions, the system 10 may also include an oil desiccation system 120.

Unlike other commercially available systems, the vaporized hydrogen peroxide system 10 operates at reduced pressure, which causes the feed solution of hydrogen peroxide in water to vaporize and occupy the vessel in the gas phase, based on the principles of Raoult's law and Dalton's law of partial pressures. As will be discussed in greater detail below, the pressure within a sterilization chamber is reduced, causing a solution of hydrogen peroxide and water to vaporize and occupy the vessel in the gas phase. By controlling the absolute pressure within the chamber, the relative concentration of vaporized hydrogen peroxide compared to other gases, such as water vapor, oxygen, and nitrogen, can be controlled. Raoult's law also dictates that the partial pressure of the hydrogen peroxide vapor can be controlled with the concentration of the hydrogen peroxide feedstock. The system 10 operates using a 3% hydrogen peroxide solution 12 at room temperature.

Figure 2:
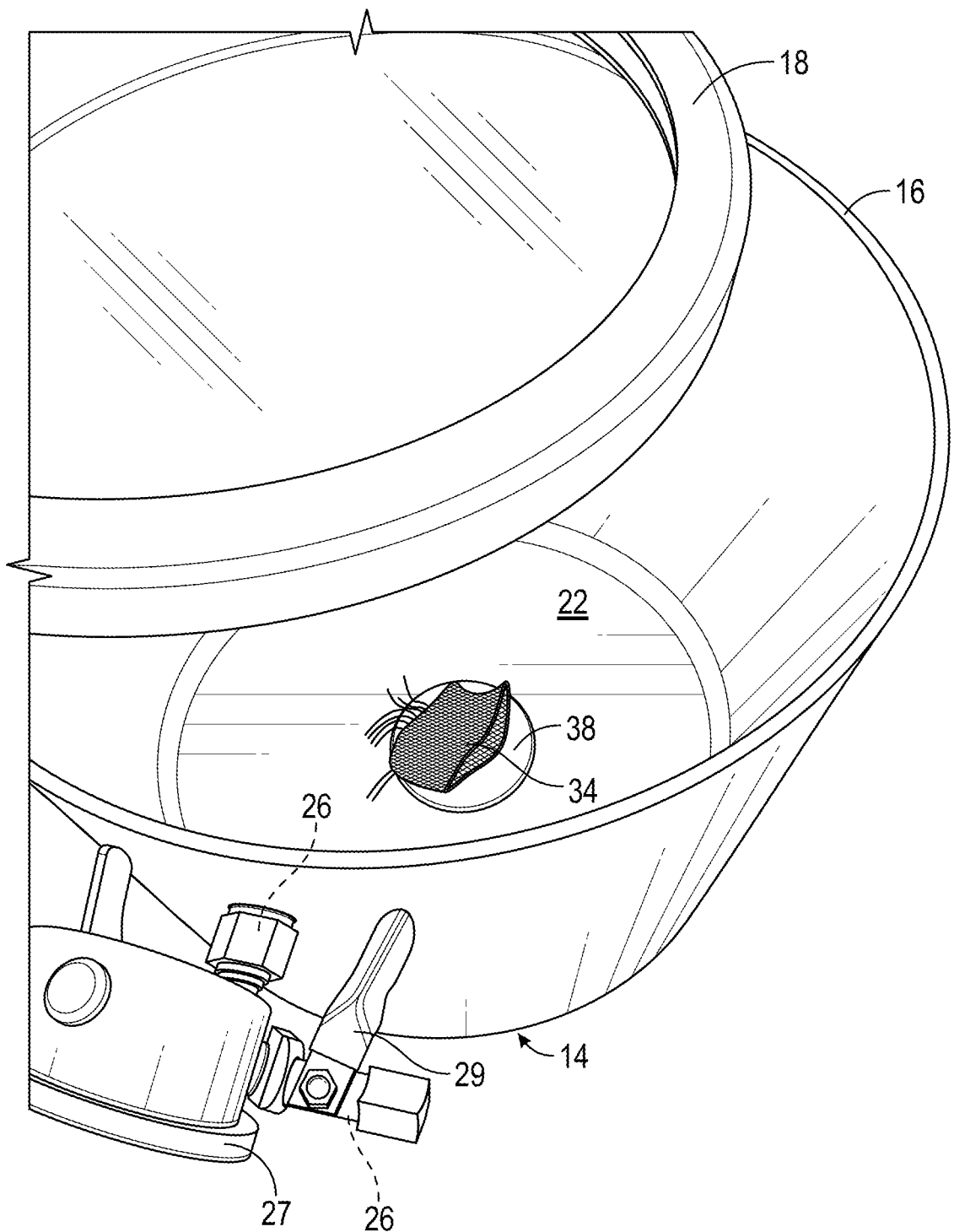
FIG. 2 is a detailed view of the vessel of FIG. 1.

FIGS. 1-2 illustrate the vessel 14 for vaporizing hydrogen peroxide in greater detail. The vessel 14 includes a body 16 and a lid 18 (e.g., closure member). The body 16 defines a sterilization chamber 22, and the lid 18 selectively engages the body 16 to close and seal the sterilization chamber 22. The lid 18 can be constructed from a translucent material (e.g., glass) and has a sealing member (e.g., a gasket) for sealing the sterilization chamber 22. The sealing member creates an air-tight and water-tight seal. Materials to be sterilized or disinfected may be positioned in the sterilization chamber 22. The materials may include industrial, medical, consumer or other types of goods and products. For example, medical supplies and personal protective equipment, such as masks or re-usable medical equipment may be placed in the sterilization chamber 22.

An intake manifold 24 is coupled to the body 16. The intake manifold 24 includes a first end and a second end opposite the first end [[24a]]. The intake manifold 24 has a first conduit 25 extending therethrough between the first and second ends and a second conduit 26 that is in communication with the first conduit 25. The second conduit 26 of the intake manifold 24 is in selective communication with the sterilization chamber 22. The intake manifold 24 includes a measurement device 27 (e.g., a pressure gauge) configured to measure pressure in the conduits 25, 26 (and therefore the sterilization chamber 22), a first valve 28 (e.g., a vacuum valve), and a second valve 29 (e.g., an atmospheric valve). The first and second valves 28, 29 may be selectively opened and closed to allow fluid flow through all or part of the first conduit 25 and the second conduit 26. In some constructions, an air intake filter may be positioned adjacent to the second end and the second valve.

Figure 3:
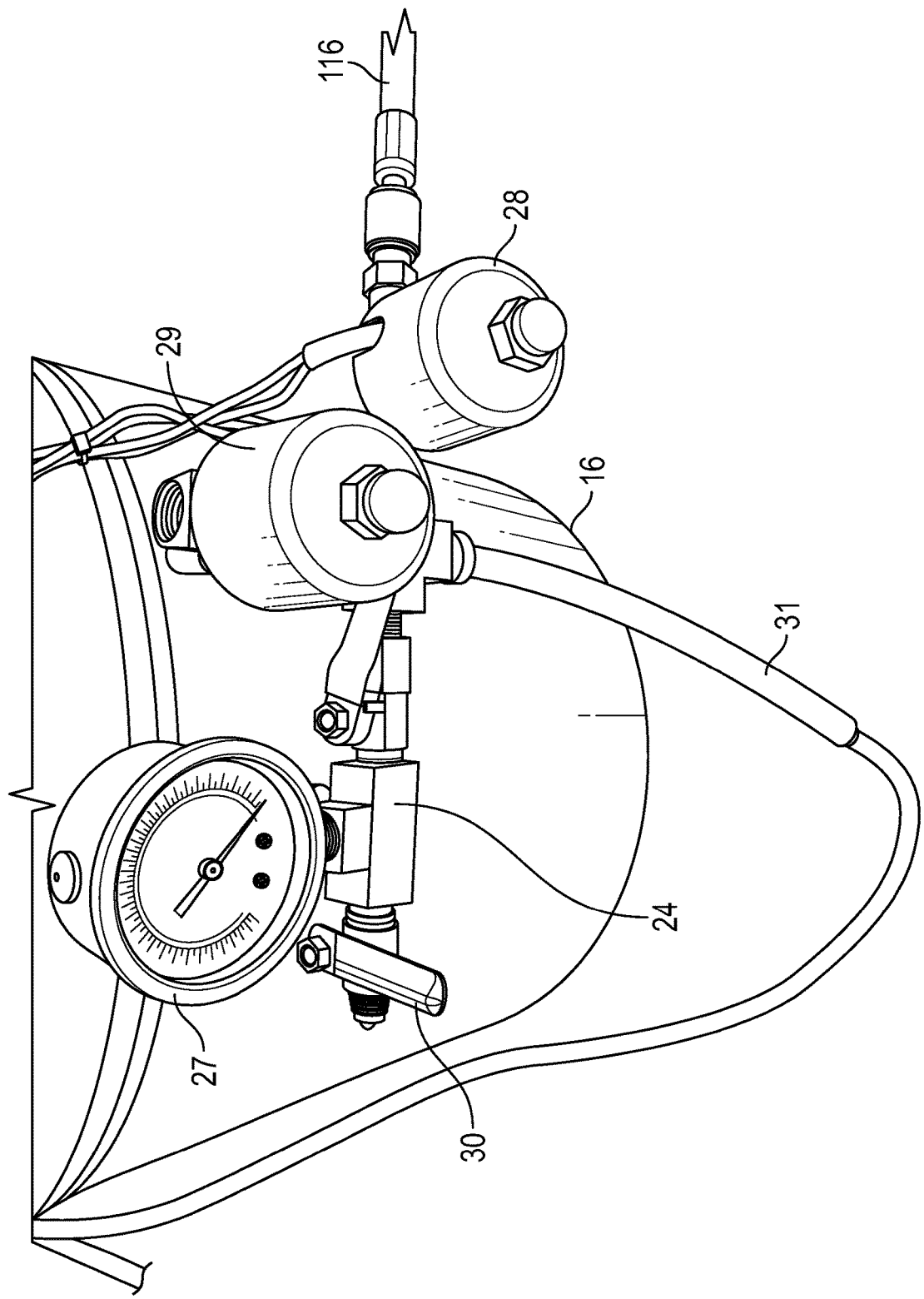
FIG. 3 is a detailed view of the vessel of FIG. 1 including another manifold.
Figure 4:
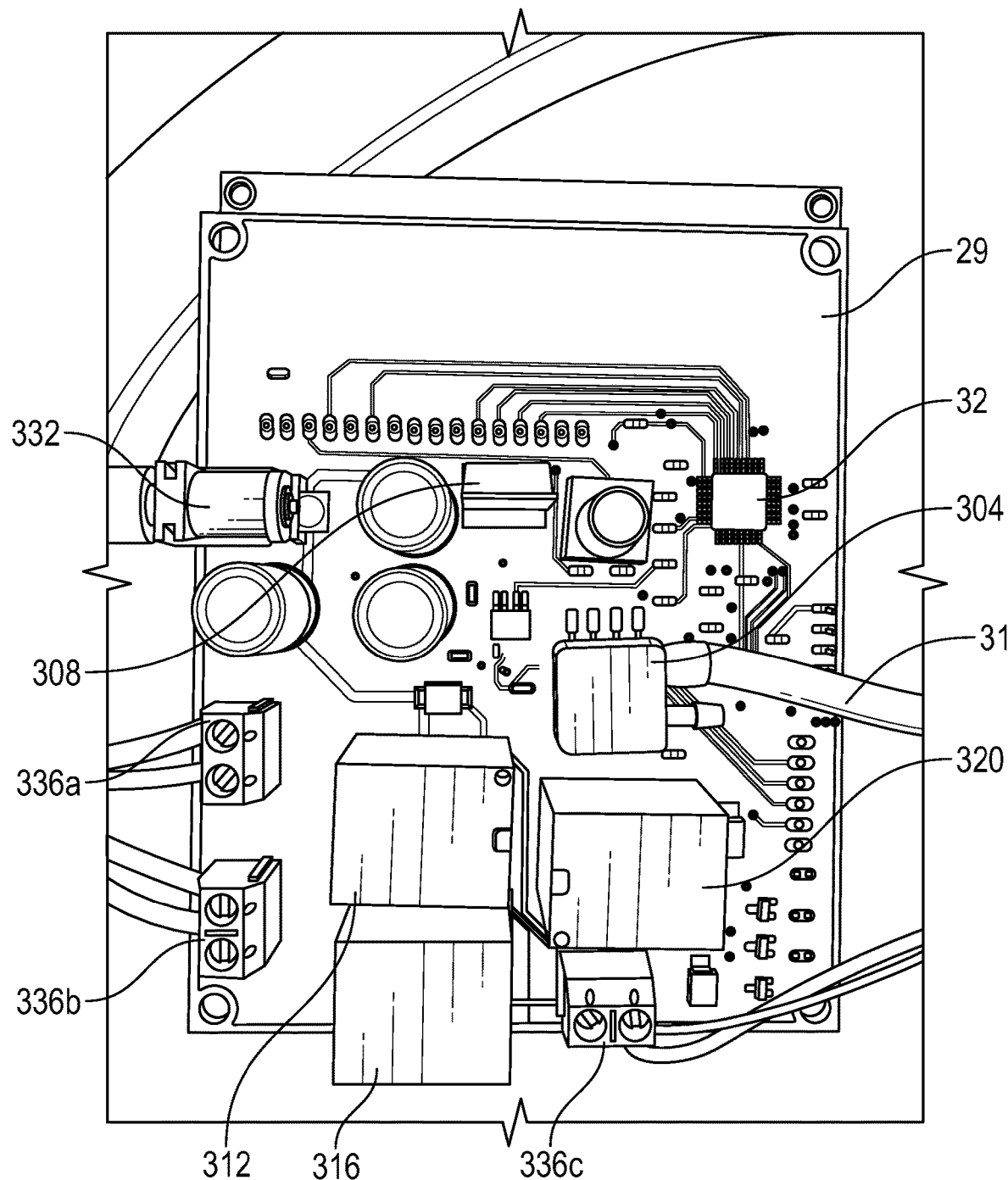
FIG. 4 is a schematic view of a printed circuit board for use with the manifold of FIG. 3.

In some constructions, as shown in FIGS. 3-4, the valves 28, 29 of the intake manifold 24 may be automated valves. That is, the first valve 28 may be a first solenoid valve (e.g., a vacuum supply solenoid valve) and the second valve 29 may be a second solenoid valve (e.g., atmospheric air solenoid valve). Moreover, the intake manifold 24 may include a manual release valve 30 and a differential pressure transducer conduit 31. The first and second solenoid valves 28, 29 are in electrical communication with a controller 32, as will be discussed in greater detail below.

A non-reactive fiber matrix 34 is positioned within the vessel that is configured to accelerate the rate of vaporization of a hydrogen peroxide solution 12 (FIG. 1) introduced into the closed sterilization chamber 22. The non-reactive fiber matrix 34 may be formed from woven fiberglass, nonwoven fiberglass, mineral wool, or other suitable materials. For example, the non-reactive fiber matrix 34 may include a woven fiberglass cloth mat, a nonwoven fiberglass cloth mat, or some other material that has high surface area, high wicking capability, and low reactivity to hydrogen peroxide. In the illustrated constructions, the non-reactive fiber matrix 34 includes several layers (e.g., three layers, although more or less would also be suitable). To this end, the non-reactive fiber matrix is a tri-folded 5 cm by 15 cm non-reactive fiber matrix 34, which creates the layers. The non-reactive fiber matrix 34 may be positioned and constrained within a receptacle 38 that is positioned within the sterilization chamber. In the illustrated constructions, the receptacle 38 is positioned at a center of a bottom surface of the vessel 14 within the sterilization chamber 22. The hydrogen peroxide solution 12 may be introduced into the vessel 14, and specifically into the receptacle 38, with the non-reactive fiber matrix 34. Therefore, the hydrogen peroxide solution 12 may wick into the non-reactive fiber matrix 34 by capillary action.

Figure 6:
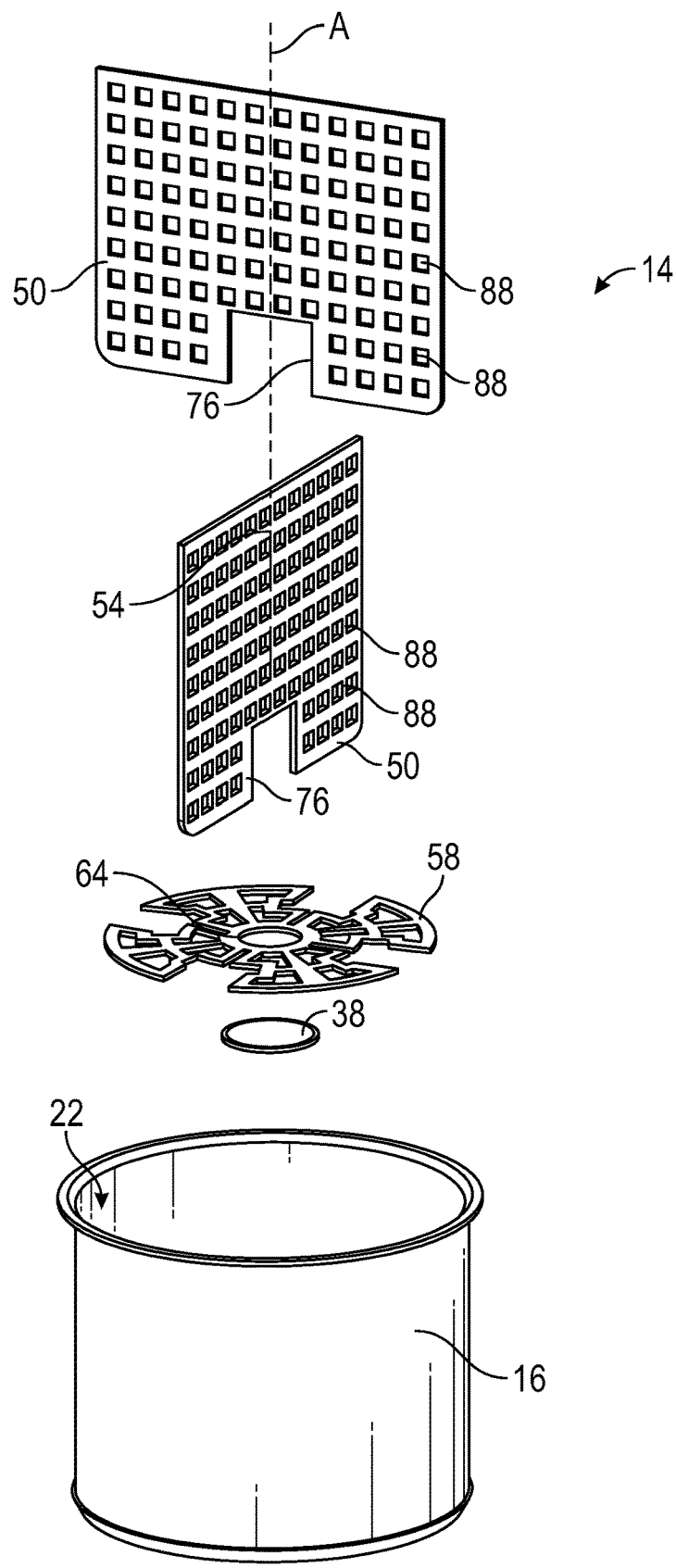
FIG. 6 is an exploded view of the vessel of FIG. 1 and including a support assembly according to one construction.
Figure 7:
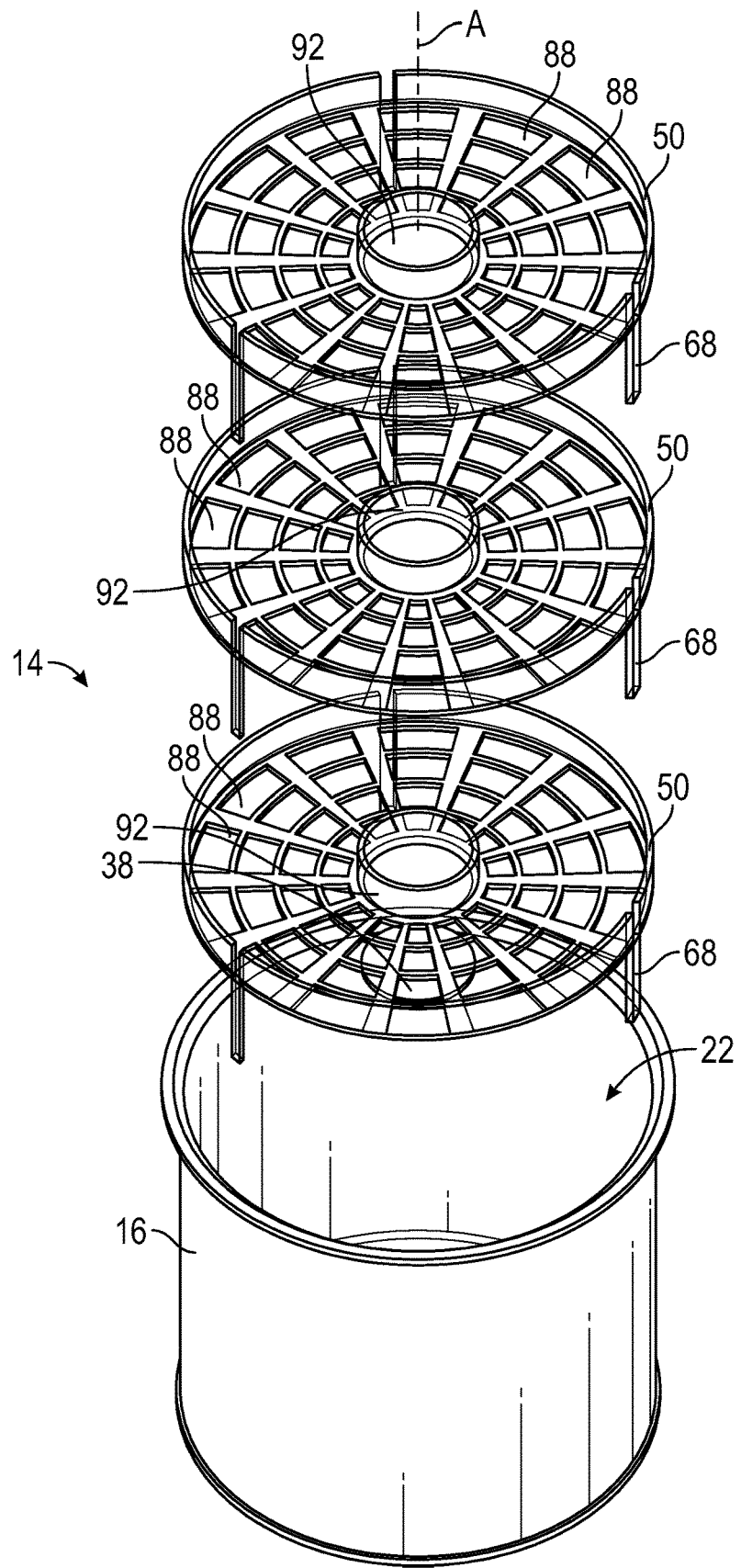
FIG. 7 is an exploded view of the vessel of FIG. 1 and including a support assembly according to another construction.
Figure 8:
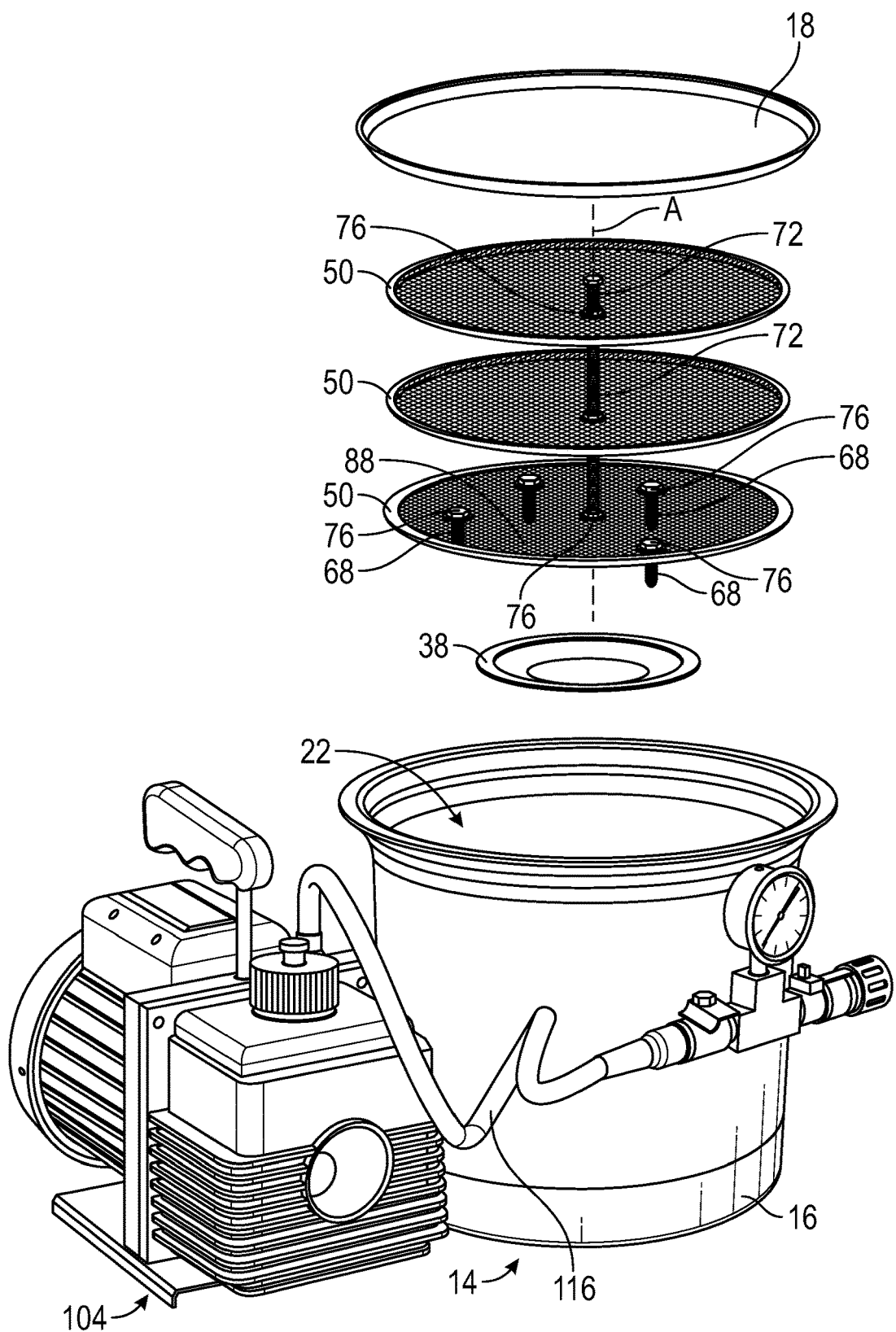
FIG. 8 is a schematic view of the sterilization system of FIG. 1 including a support assembly according to another construction.

As shown in FIGS. 6-8, the vessel 14 may include a support assembly (e.g., an item loader) including one or more plates or dividers 50 that divide or separate the storage chamber 22 into sterilization compartments. The one or more dividers are used to support and separate the treated items, ensuring adequate gas diffusion.

In the construction of FIG. 6, the dividers 50 extend longitudinally within the body 16, and separate the sterilization chamber 22 into four sterilization compartments, for example. As shown, a first divider 50 is removably coupled to a groove 54 of a second divider 50. The first and second dividers 50 may be coupled to and stabilized by a base member 58 positioned within the body 16. The base member 58 is positioned above the receptacle 38 and includes a plurality of apertures 64 that allow fluid communication between the nonreactive fiber matrix 34 and the storage compartments.

In the constructions of FIGS. 7 and 8, the dividers 50 extend transversely within the body 16 and each define a support surface. As shown, a first divider 50 is positioned adjacent to the receptacle 38, a second divider 50 is positioned between the first divider 50 and a third divider 50, and the third divider 50 is positioned adjacent to a top of the body 16. In other or additional embodiments, there may be more or fewer dividers 50. As shown, the dividers 50 are supported relative to one another and relative to the body 16. In the illustrated constructions, the dividers 50 are substantially circular, although in other embodiments the dividers 50 may have other suitable shapes (e.g., rectangular, square, polygonal, etc.).

With respect to the construction of FIG. 7, each of the dividers 50 include one or more projections 68 that stabilize the corresponding divider 50 relative to the body 16 and other dividers 50. The projections 68 of the first divider 50 are supported by a bottom surface of the body 16, the projections 68 of the second divider 50 are supported by the first divider 50, and the projections 68 of the third divider 50 are supported by the second divider 50. Moreover, the projections are arranged about a perimeter of each divider. In the illustrated construction, the three projections 68 are equidistant about the perimeter. That is, adjacent projections 68 are positioned at a 120 radial angle relative to the adjacent projections. In other constructions, there may be more or fewer projections that are spaced relative to one another in other suitable ways. In some constructions, the body 16 and the dividers 50 may have grooves that receives and secure the projections 68.

With respect to the construction of FIG. 8, the first divider 50 includes one or more projections 68 that stabilize the first, second, and third dividers 50 relative to the body, and the first, second, and third dividers 50 are coupled by a fastener 72. As shown in FIG. 8, the projections 68 are fasteners (e.g., bolts) that include a first end and a second end opposite the first end. The projections 68 each extend through a hole or aperture in the first divider 50 such that the first end is positioned adjacent a first surface of the first divider and the second end is spaced apart from the first divider 50. Each of the projections 68 is secured to the first divider by one or more nuts, washers, and/or other coupling devices 76, for example. In other constructions, the projections 68 may formed in other ways. In the illustrated construction, the first divider 50 may also be spaced apart from a closed end of the body 16 by a first distance, which is equal to a length of the bolt. In the illustrated embodiments, the length of the bolt is 2 inches (e.g., about 5.1 cm±0.5 cm). In other constructions, the first divider 50 may be spaced at different distances relative to the closed end of the body 16. That is, the projections 68 may have any suitable length to support the support assembly above the closed end of the body 16. The projections 68 of FIG. 8 are arranged inward from the perimeter of the first divider 50. In the illustrated construction, the three projections 68 are equidistant about the perimeter. That is, adjacent projections 68 are positioned at a 120 radial angle relative to the adjacent projections. In other constructions, there may be more or fewer projections that are spaced relative to one another in other suitable ways.

Further with respect to FIG. 8, the dividers 50 each include a central aperture or hole that extends through the support surface thereof. The apertures are aligned with one another along a common axis A. The fastener 72 includes a first end that is positioned opposite the support surface of the first divider and a second end that is positioned adjacent to the support surface of the third divider. The fastener 72 extends through respective apertures of each of the dividers 50. In the illustrated construction, the fastener is an all-thread bolt measuring 8 inches, but in other configurations, the fastener may have other suitable configurations and lengths. In some constructions, the dividers 50 may be coupled by a plurality of fasteners 72 that are consecutively relative to one another rather than a single fastener. Each divider 50 is coupled to the fastener 72 via nuts or other coupling devices 76 positioned on opposite sides of the support surface of the respective divider 50. In the illustrated construction, the dividers 50 are coupled at equal intervals relative to one another along the fastener 72. That is, each the first, second, and third dividers 50 are spaced apart from the adjacent dividers by a second distance (e.g., 6.5 cm). In other constructions, the dividers 50 may be spaced at different distances relative to one another. In the illustrated construction, the first divider 50 may also be spaced apart from a closed end of the body 16 by the second distance. In other constructions, the first divider 50 may be spaced at different distances relative to the closed end of the body 16. The support assembly may include a handle 90 to assist the user in grasping and moving the support assembly. In the illustrated construction, an extra fastener is positioned at or adjacent the third divider, and in this case, at or adjacent the second end of the fastener.

In some constructions, the dividers 50 are formed as perforated plates and therefore include a plurality of apertures 88 to allow fluid communication between the sterilization compartments. Moreover, in some constructions, the dividers 50 may each include a cutout or opening 92 that is aligned with or surrounds the non-reactive fiber matrix 34.

With renewed reference to FIG. 1, the vacuum source 104 is a vacuum pump (e.g., a rotary-vane vacuum pump, HVAC-type rotary-vane vacuum pump), although the vacuum source may be any suitable low-cost, widely available vacuum source 104. The hydrogen peroxide solution 12 is 3% hydrogen peroxide solution and may be introduced into the vessel 14 by any suitable method. Although not shown in FIG. 1, the heat source (e.g., a heat pad) may be in thermal communication with the vessel 14. Specifically, the heat source may be positioned below the vessel 14. The conduit 116 allows fluid communication among the dispenser, the vessel 14, and the vacuum source 104. Examples of the heat source and the dispenser are discussed in greater detail below with respect to FIG. 8. In some constructions, the dispenser may include one or more valves, discussed in greater detail with respect to the system of FIG. 8, below. When the vacuum source 104 is a vacuum pump that requires clean lubricating oil to operate properly, the oil desiccation system 120 may be employed. The oil desiccation system 120 removes moisture and condensate (e.g., water, hydrogen peroxide, etc.) from the oil of the vacuum pump.

Figure 5:
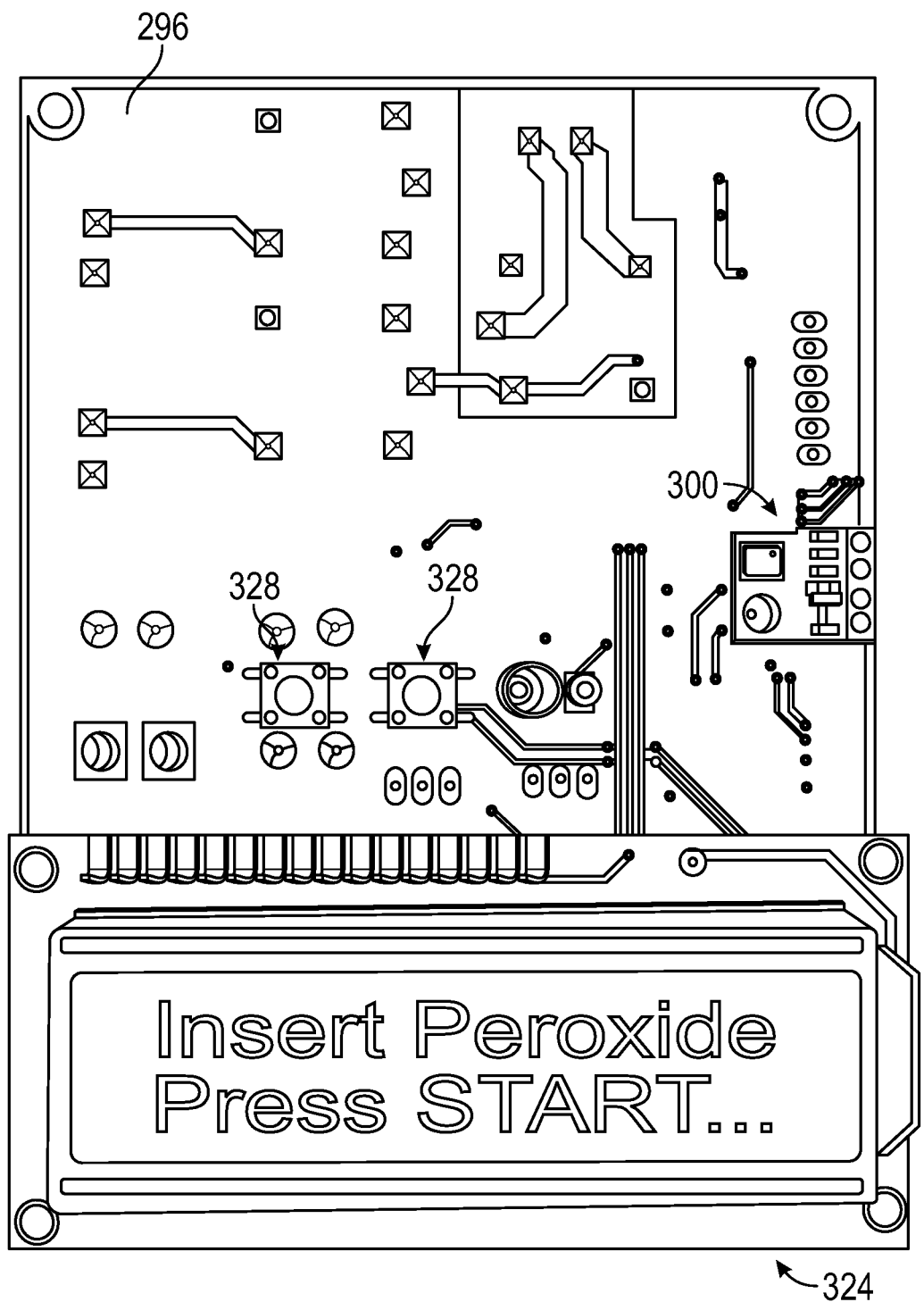
FIG. 5 is a schematic view of the printed circuit board in communication with a display.

As noted above, the system 10 may further include a controller 32 to control the vacuum source 104 and the first and second solenoid valves 28, 29 based on sensed information from one or more sensors. With renewed respect to FIGS. 3-5, a printed circuit board 296 supports the controller 32. Also, supported by the printed circuit board 296 and in communication with the controller are a first sensor 300, a second sensor 304, a voltage regulator 308, a first relay 312, a second relay 316, a third relay 320, a display 324, and one or more actuators 328. A power source 332 (e.g., an AC or DC power source) may power the controller 32. The first solenoid valve 28, the second solenoid valve 29, and the vacuum source 104 are in communication with the controller 32 via terminals blocks 336a-336c. The first solenoid valve 28 controls the vacuum source 104 and the second solenoid valve 29 controls the atmospheric air intake. The first relay 312 is in communication with and controls the first solenoid valve 28. The second relay 316 is in communication with and the controls the second solenoid valve 29. The third relay 320 is in communication with and controls the vacuum source 104. The display 324 may be an LCD display configured to assist and instruct the user during use of the system 10.

In the illustrated construction, the first sensor 300 is an ambient temperature sensor configured to detect an ambient temperature surrounding the system 10. The second sensor 304 is a pressure transducer that is in communication with the pressure transducer conduit 31. Moreover, one or more sensors (not shown) may be positioned within the sterilization chamber 22 and/or elsewhere in the systems 10, 10' and may be configured to communicate with the controller 26. The one or more sensors may provide feedback to the controller 32 such that the controller 32 may adjust temperature and/or valve position and/or hydrogen peroxide vapor output to maintain a pre-determined internal condition and/or level of hydrogen peroxide vapor within the sterilization chamber 22. That is, the controller 32 monitors characteristics (e.g., ambient temperature, atmospheric pressure, differential air pressure (e.g., the difference in pressure between the inside and the outside of the chamber 22), and absolute pressure within the vacuum chamber 22) via sensed information from the ambient temperature sensor 300, the pressure transducer 304, and the other sensors to ensure that the conditions are suitable for effective vaporized hydrogen peroxide sterilization. The sensor measurements and adjustment of hydrogen peroxide vapor levels within the chamber 22 may be in communication with a timer (e.g., a software timer) in communication with the controller 32 such that the materials within the sterilization chamber 22 are exposed to the pre-determined level of hydrogen peroxide for a pre-determined amount of time. Although not shown, the status of the timer may be displayed on the display 324. The use of a controller 32 may allow the methods described herein to be automated.

Figure 9:
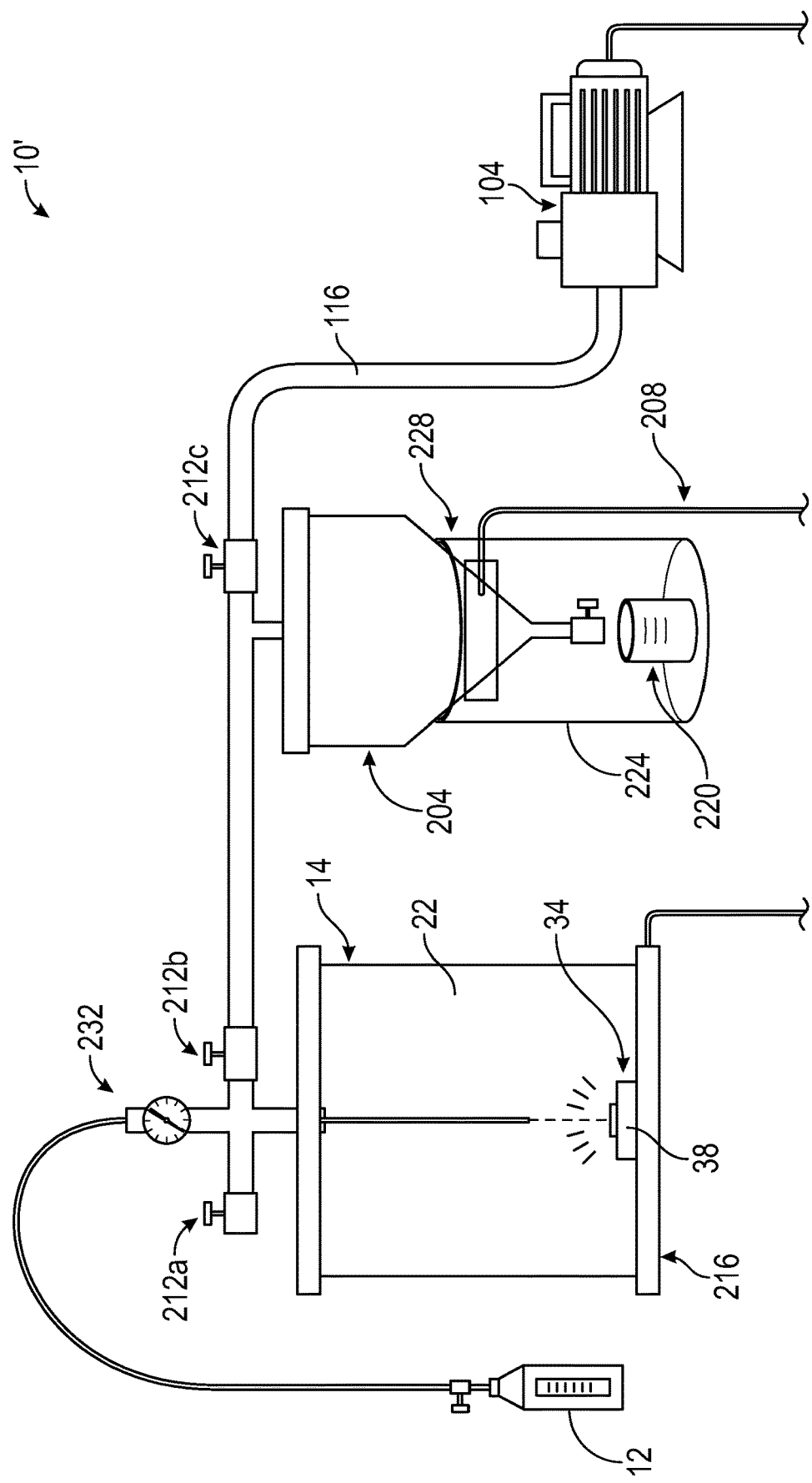
FIG. 9 is a schematic view of a sterilization system according to another construction.

A sterilization system 10' according to another constructions is shown in FIG. 9. The sterilization system 10' of FIG. 9 is similar to the sterilization system 10 of FIG. 1, so like reference numerals noted with like structure and only the differences will be discussed herein. The sterilization system 10' includes a purge tank 204 that captures hydrogen peroxide vapor and/or other vapors such as water vapor. In some constructions, as shown here, a condenser 208 may include the purge tank 204 and a plurality of valves 212a-212c. A heat source 216 (e.g., a heat pad) is in thermal communication with the vessel 14. In the illustrated construction, the heat source 216 is positioned below the vessel 14. The purge tank 204 includes a condensate drain positioned 220 in (or otherwise in fluid communication) with a container 224 and a cooling source or jacket 228 in thermal communication with the purge tank 224. The conduit 116 allows fluid communication among the dispenser 232, the vessel 14, the condenser 208, and the vacuum source 104. The plurality of valves 212a-212c are positioned along the conduit 116 to control the fluid flow among the dispenser 232, the vessel 14, the condenser 208, and the vacuum source 104. A first of the plurality of valves 212a is an atmospheric valve, a second of the plurality of valves 212b is a condenser isolating valve (e.g., a purge tank isolating valve), and a third of the plurality of valves 212c is a vacuum source isolating valve (e.g., a pump isolating valve).

As noted throughout, the systems 10, 10' operate on the principle of Raoult's law and Dalton's law of partial pressures. The pressure within a negative-pressure vessel 14 is lowered to a sufficient level to allow the hydrogen peroxide solution 12, which includes water, to vaporize and occupy the vessel 14 in the gas phase. By controlling the absolute pressure within the sterilization chamber 22, the relative concentration of vaporized hydrogen peroxide compared to other gases, such as water vapor, oxygen, and nitrogen, can be controlled. Raoult's law specifies that the vapor pressure of the hydrogen peroxide vapor will depend on the concentration of hydrogen peroxide in the hydrogen peroxide solution 12 introduced to the vessel 14, which gives an additional control parameter for controlling the partial pressure of hydrogen peroxide vapor. Additionally, adjustment of the temperature within the sterilization chamber 22 will also influence the partial pressure of hydrogen peroxide vapor. Moreover, the nonreactive fiber matrix 34 serves to accelerate the vaporization of hydrogen peroxide solution 12 by providing surface area and wicking, which facilitates exposure of the hydrogen peroxide solution 12 to the chamber atmosphere under the specified temperature and pressure conditions of the vessel 14. As noted above the nonreactive fiber matrix 34 is formed from a material that has low reactively with or will not react with the hydrogen peroxide solution 12, which prevents the consumption of hydrogen peroxide during dispensing, and also avoids creating potentially hazardous conditions where explosive decomposition of concentrated hydrogen peroxide could occur in the presence of a more reactive substrate. The vacuum source 104 is used to evacuate the sterilization chamber 22 to adequate vacuum level.

Upon evacuation of the sterilization chamber 22, the rate of vaporization of hydrogen peroxide solution 12, and therefore the rate at which partial pressure equilibrium is achieved, is thereby increased substantially by the use of the non-reactive fiber matrix 34 and the large exposed surface area thereof. A rapid achievement of partial pressure equilibrium is desirable, as it allows disinfection or other processes relating to the use of vaporized hydrogen peroxide to achieve controlled concentration of hydrogen peroxide vapor more quickly than if a container of hydrogen peroxide solution 12 were simply placed in the vessel. This accelerates the rate at which these processes can be performed, and ensures that dynamic processes in which hydrogen peroxide vapor is actively consumed remain amply supplied with hydrogen peroxide vapor throughout their duration. The hydrogen peroxide vapor can thus be used to sterilize or disinfect the material positioned within the sterilization chamber 22. The dividers 50, and the apertures 88 thereof, may be used to separate and ensure adequate gas diffusion into items being treated.

Figure 10:
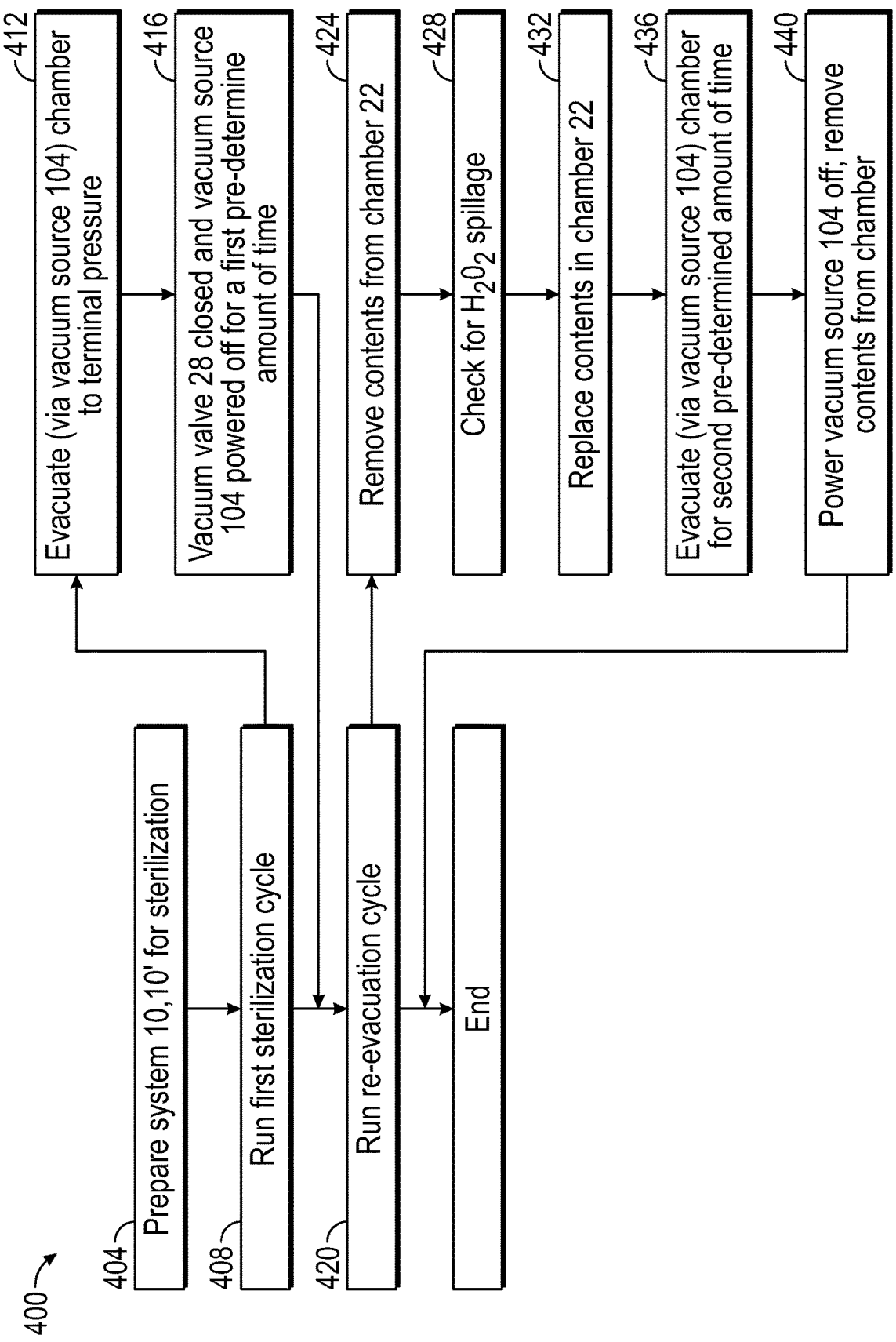
FIG. 10 illustrates a method of sterilizing one or more items using the sterilizations systems of FIGS. 1 and 7.
Figure 11:
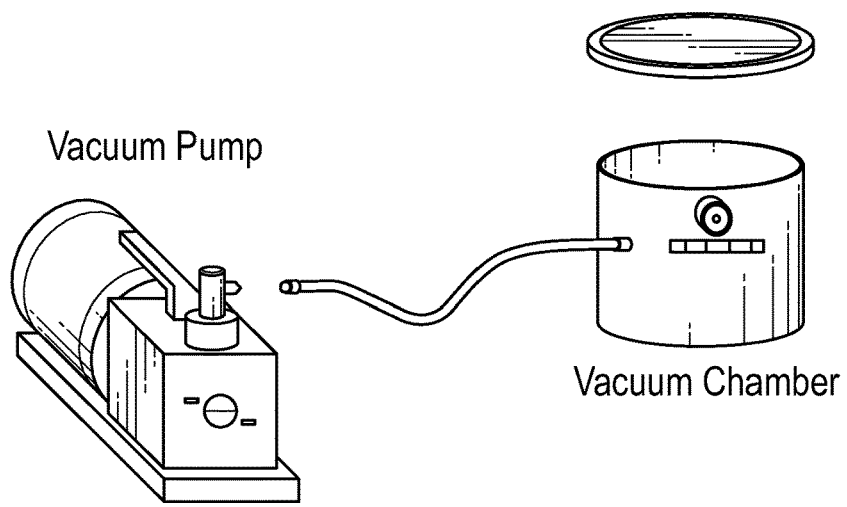
FIG. 11 is a schematic view of one of the steps of the method of FIG. 10.
Figure 12:
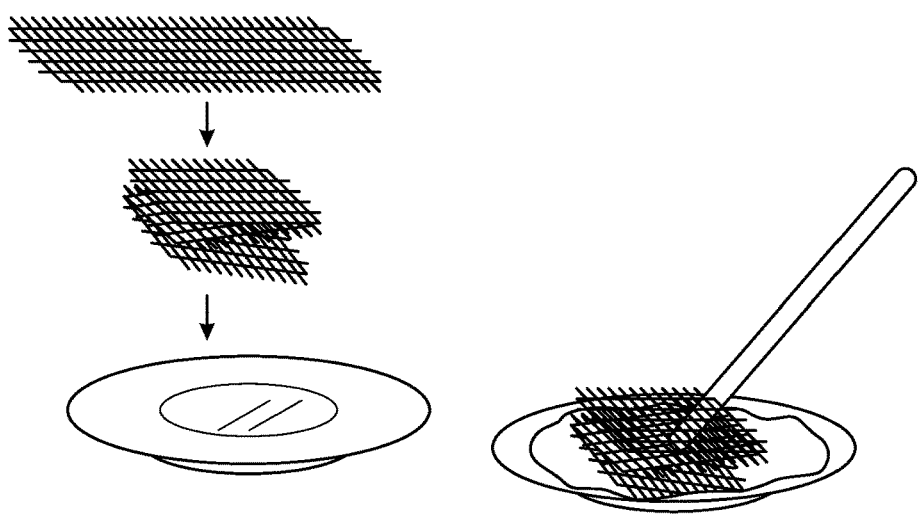
FIG. 12 is a schematic view of one of the steps of the method of FIG. 10.
Figure 13:
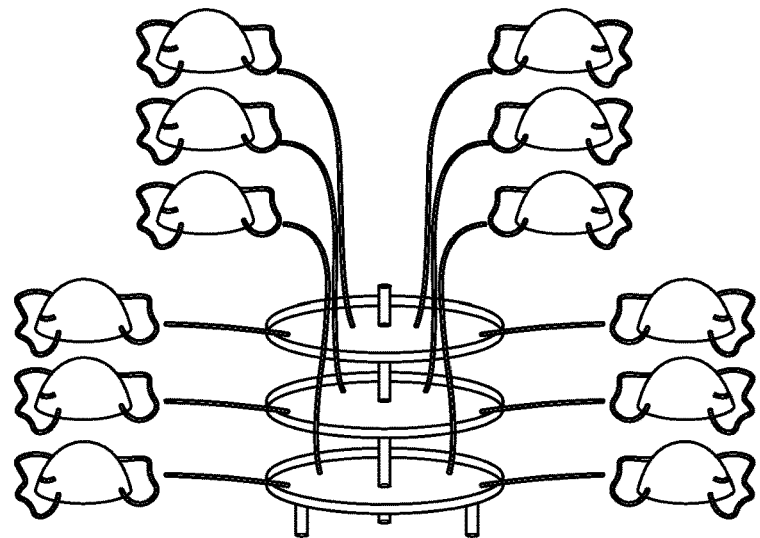
FIG. 13 is a schematic view of one of the steps of the method of FIG. 10.

With respect to FIG. 10, the method 400 for use of the systems 10, 10' includes preparing the system for sterilization, at step 404 and FIGS. 11-13. That is, as shown in FIG. 11, the vacuum source 104 is coupled via the conduit 116 to the intake manifold 24 of the vessel 14. In some constructions, the sterilization chamber 22 and the vacuum source 104 should be positioned in an area having an ambient temperature of at least 20 degrees C. The vacuum source 104 should have an appropriate oil level. Moreover, the atmospheric valve 29 should be closed and a vacuum valve 28 opened. Further with respect to FIG. 12, this step further includes combining the hydrogen peroxide solution 12 with a nonreactive fiber matrix 34 within the receptacle 38, which is positioned in the chamber 22 of the vessel 14. The receptacle 38 may be positioned centrally in the vessel 14 and the hydrogen peroxide solution 12 (e.g., 10 mL of 3% hydrogen peroxide solution) may be dispensed into the vessel 14 and onto the receptacle 38 and nonreactive fiber matrix 34 (via a suitable method such as pouring the solution from a 50 mL beaker). Generally, 10 mL of hydrogen peroxide solution is suitable for the illustrated vessel 14, which accommodates a 5-gallon chamber 22, but the amount of hydrogen peroxide solution may range from 5 mL to 100 mL in other constructions, depending on size of the chamber 22 accommodated within the vessel 14. The concentration of the hydrogen peroxide in solution should be at least at least 3%. Although percentages of hydrogen peroxide in solution as high as 50% may be useable without concerns about chemical stability, the range of percentages of hydrogen peroxide in solution is typically between 3% and 8%. The nonreactive fiber matrix 34 may be saturated with the solution 12 (using a stir rod or wood splint). This step also includes, positioning the items to be treated on the support surfaces of the dividers 50 of the support assembly, prior to the support assembly being positioned in the vessel 14 (FIG. 13). Preferably, if the treated items are respirators, they should be placed onto the support surfaces of the dividers 50 with the seal facing downwards, flat on the support surface, and the largest area of the respirator faced upwards. If possible, respirators and other items to be treated should be placed into self-sealing sterilization pouches before placement in the systems 10, 10' to prevent decontamination after treatment. The populated support assembly is then lowered into the sterilization chamber 22, above the non-reactive fiber matrix 34. The lid 18 provided with the vessel 14 is placed onto the top of the body 18 to cover the same. The silicone gasket of the lid 18 should be uniform all around the lid 18 and is not buckled or loose in any region. Moreover, the lid 18 should be centered relative to body 16.

The method for use of the systems 10, 10' further includes subjecting the items to be treated to a first sterilization cycle of vaporized hydrogen peroxide shown at 408. At step 412, the first cycle includes evacuating, by the vacuum source 104, the sterilization chamber 22. When the vacuum source 104 is a rotary-vane vacuum pump, the pump evacuates (e.g. pulls a vacuum) on the chamber 22 to remove the atmosphere and create a vacuum. In some cases, the oil in the vacuum source 104 can become contaminated with moisture (e.g., $H_2O_2$ or $H_2O$, etc.). The desiccation system 120 may remove this moisture contamination from the oil. In one construction, the chamber 22 may be evacuated by the running the vacuum source 104 for a first predetermined amount of time (e.g., three to five minutes) until the absolute pressure in the chamber 22 is below the terminal pressure (e.g., between 21 torr and 35 torr for 3% hydrogen peroxide solution). The terminal pressure (in inches of Hg relative) may be computed using the equation:

$$Pvac = -(Pambient - 35)/25.4$$

The Pvac is the relative pressure that must be achieved in the chamber 22 in inches of Hg and Pambient is the barometric pressure of the region in which the system is being operated, in mm of Hg).

In the illustrated construction, the system 10 should be operated at 28 torr absolute pressure. The terminal pressure, and therefore the terminal vacuum level, will depend on the ambient pressure (altitude), and may need to be corrected for higher or lower altitude facilities.

Once the terminal pressure in the system is achieved, the vacuum valve 28 is closed before turning the vacuum source 104 off and waiting a first pre-determined treatment time (e.g., 60 minutes for sterilization of N95 respirators) to achieve a recommended dose of vaporized hydrogen peroxide exposure (e.g., step 416). During the first pre-determined treatment time, the vacuum created in the chamber 22 vaporizes the hydrogen peroxide in the hydrogen peroxide solution 12 to sterilize the one or more materials. For N95 respirators, orienting the N95s within the chamber so the largest area of the respirator faces upward allows for maximum exposure to vaporized hydrogen peroxide and higher quality disinfection. The method further includes reintroducing air by opening the atmospheric valve 28 in a well-ventilated space. Then the lid 18 may be removed from the body 16. Then, the support assembly containing the treated items can be removed from the body 16. This process may be repeated to subject to the treated items to multiple sterilization cycles.

The dosage required for the systems 10, 10' to reach is dependent on the device being decontaminated and what sterility assurance level is required. N95 respirators should be sterilized due to their proximity to the respiratory tract of health care professionals. According to the American National Standard ANSI/AAMI ST67, a $6\text{-}\log_{10}$ reduction of microorganisms is required for sterilization of the majority of medical devices, which is extended to N95 respirators. Table 1, below, shows the dosage recommendations for achieving sterilization using the systems 10, 10' herein.

TABLE 1

Dosage chart containing pressure level and phase times in order to reach a 6-log 10 reduction of biological contaminants.

| | Suggested Use Cases | Hg Achieved | Gassing Phase | Dwell Phase | Aeration Phase |
|---|---|---|---|---|---|
| Sterilization ($6\text{-}\log_{10}$ reduction) | N95 Respirators and other filtering facepiece respirators, surgical masks, other PPE (specifically required for healthcare facilities) | Vacuum level indicated by $p_i = p_1 * x_i$ | 3-5 min (until vacuum level indicated by $p_i = p_1 * x_i$ reached) | 60 min | 15 min |

In Table 1, the gassing phase is the time required for the chamber to reach the recommended pressure, the dwell phase indicates the length of vaporized hydrogen peroxide contact suggested for N95 masks and other use cases when the chamber is left undisturbed, and the aeration phase refers to the process of reintroducing atmospheric air into the chamber to prevent off-gassing from PPE during use.

The method may further include a re-evacuation cycle, at 420. In this case, after the first sterilization cycle is completed, the support assembly containing the treated items are removed from the vessel 14 and the receptacle 38 and nonreactive fiber matrix 34 are removed from the vessel to ensure that no spilled hydrogen peroxide solution remains at the bottom of the chamber 22 (at steps 424, 428). The support assembly containing the treated items is then replaced in the vessel 14, the vessel 14 is closed by lid 18, and the chamber 22 is re-evacuated by allowing the vacuum source 104 to run for a second pre-determined amount of time (e.g., 30 min) (at steps 432, 436). The vacuum valve 28 is closed before turning of the vacuum source 104, air is reintroduced, and the treated items removed from the vessel 14 (at step 440). This cycle ensures the bulk removal of hydrogen peroxide and other volatile materials from the treated items. In some constructions, this re-evacuation cycle may be omitted if there is a desire to cause the liquid water and hydrogen peroxide to condense onto the surfaces of the materials as air is reintroduced.

The re-evacuation cycle takes the place of an aeration phase that is commonly used with processes using vaporized hydrogen peroxide. The aeration phase is a period of time between when the items are treated and when the items are used by the user, which prevents user exposure to vaporized hydrogen peroxide. According to N95 *Mask Decontamination using Standard Hospital Sterilization Technologies*, the necessary aeration time for N95 masks treated with VHP at atmospheric pressure at 750 ppm concentration is 20 minutes. The systems 10, 10' discussed herein employ the re-evacuation step, which is a vacuum drying stage that operates at 28 torr. The proposed system also utilizes a concentration that is estimated to reach a maximum value of 681 ppm by experimental measurement.

If the rate of evaporation of hydrogen peroxide from surfaces is approximated to be linearly dependent on ambient pressure, the required aeration time can be expressed in terms of the ratio of ambient pressures and the original aeration time as shown below:

$$T_{a2} = T_{a1} * \frac{P_2}{P_1}$$

where $T_{a2}$ is the aeration time at ambient pressure $P_2$ and $T_{a1}$ is the aeration time at ambient pressure $P_1$.

Furthermore, if the aeration time is assumed to be approximately linearly dependent on the concentration of vaporized hydrogen peroxide during treatment, the required aeration time can be expressed in terms of the ratio of treatment concentrations and the original aeration time as shown below:

$$T_{a2} = T_{a1} * \frac{C_2}{C_1}$$

where $T_{a2}$ is the aeration time at concentration $C_2$ and $T_{a1}$ is the aeration time at ambient pressure $C_1$.

Combining these equations accordingly, the aeration time as a function of both the ambient pressure ratios and concentration ratios between the proposed vaporized hydrogen peroxide system and existing vaporized hydrogen peroxide systems in the literature can be expressed as shown below:

$$T_{a2} = T_{a1} * \frac{C_2}{C_1} * \frac{P_2}{P_1}$$

Substituting the given values of concentration and pressure, the required aeration time in the vacuum drying process is therefore expressed in equations below:

$$T_{a2} = (20 \text{ min}) * \frac{15000 \text{ ppm}}{750 \text{ ppm}} * \frac{28 \text{ torr}}{760 \text{ torr}} = 14.73 \text{ min}$$

$$T_{a2} = (20 \text{ min}) * \frac{681 \text{ ppm}}{750 \text{ ppm}} * \frac{28 \text{ torr}}{760 \text{ torr}} = 0.669 \text{ min}$$

It requires approximately 5 minutes of vacuum time to achieve the vacuuming time to achieve the vacuum level under which this aeration time was computed using the pumps recommended in the bill of materials for this system. The total minimum vacuum pump operation time during the aeration phase is therefore approximately 5.67 minutes. Due to tolerances in the vacuum pump design and chamber temperature, a conservative recommendation for aeration time can be given as twice this value plus a margin of error, for a total recommended aeration vacuum pumping time of 15 minutes.

Figure 14A:
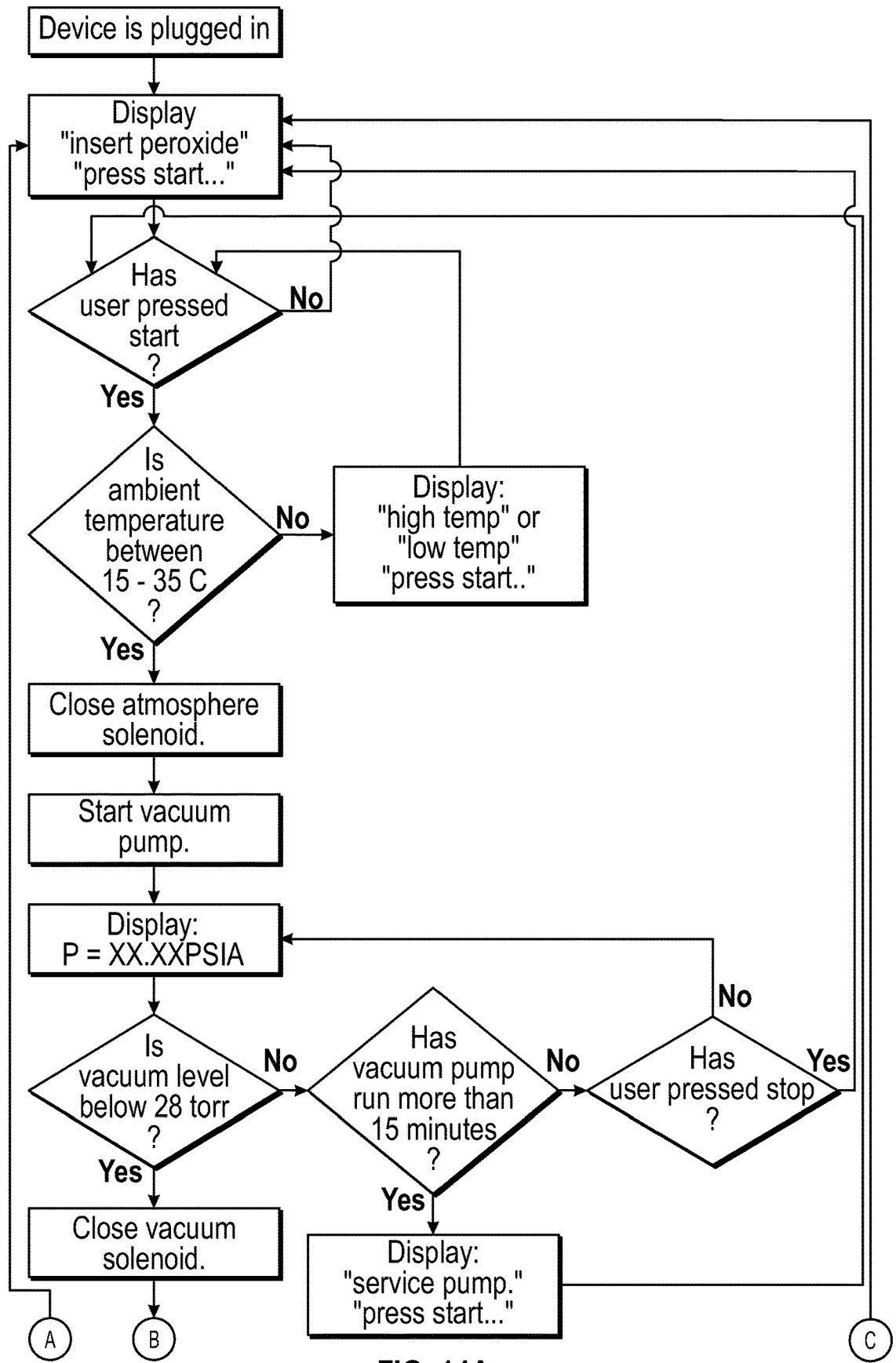
FIG. 14A illustrates a first portion of a flowchart in which the method of FIG. 10 is automated.
Figure 14B:
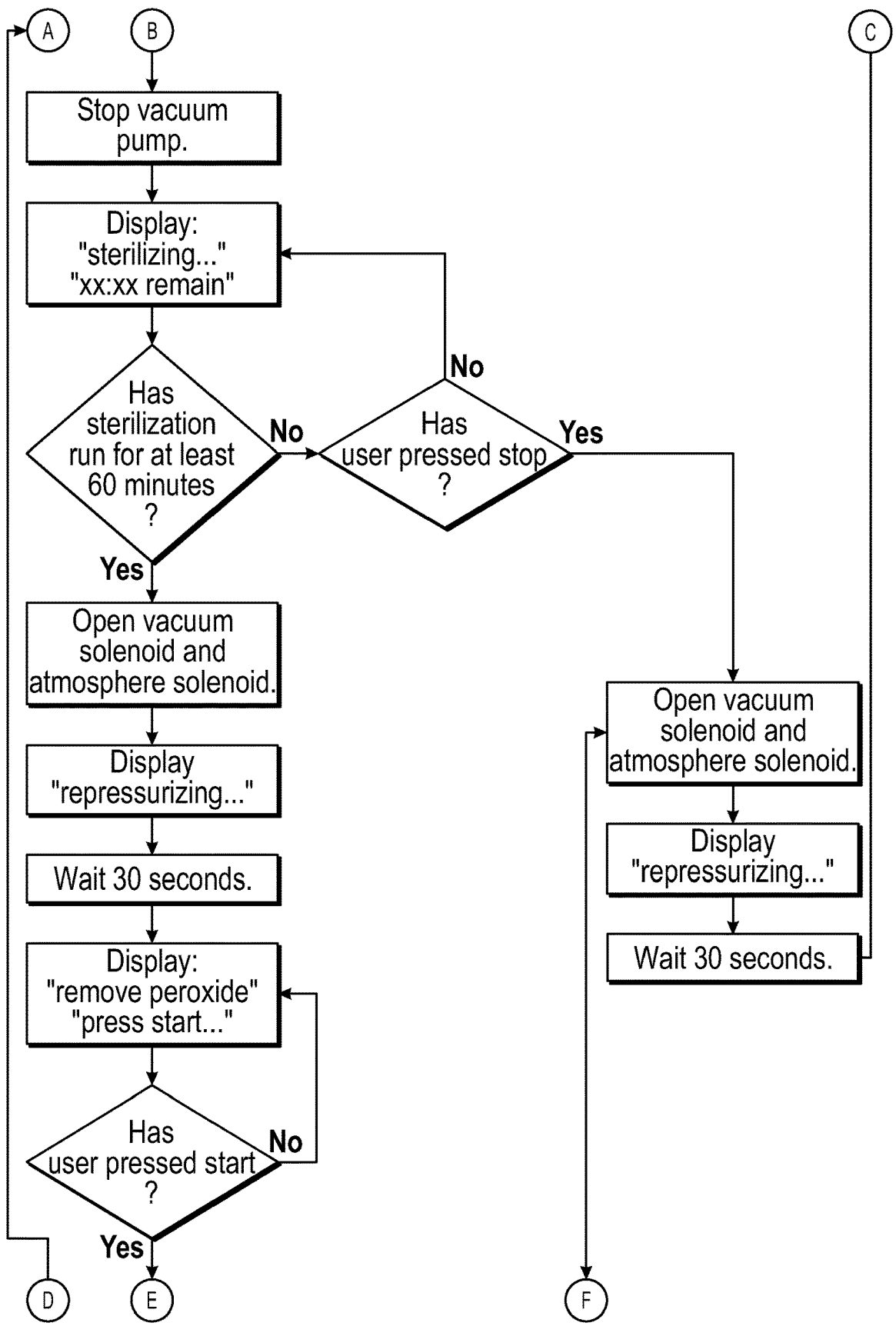
FIG. 14B illustrates a second portion of the flowchart in which the method of FIG. 10 is automated.
Figure 14C:
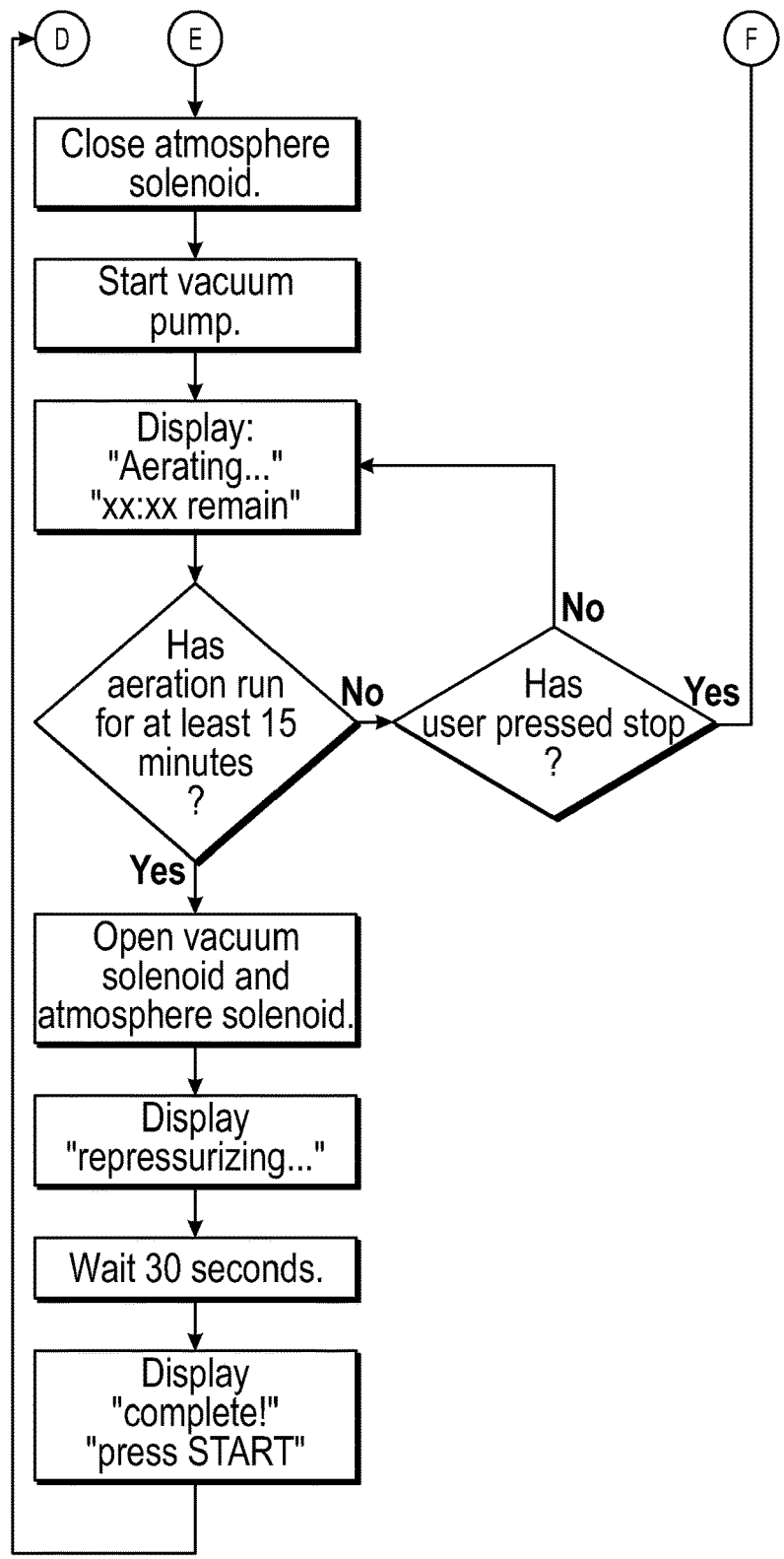
FIG. 14C illustrates a third portion of the flowchart in which the method of FIG. 10 is automated.

As shown in the flowchart of FIGS. 14A-14C, when the controller 32 is used the method 400 may be automated. The automated method may be started by actuating one of the actuators 328 (e.g., the "START" actuator) and ended (if necessary) by actuating another actuator 328 (e.g., the "STOP" actuator 328). Moreover, the display 324 may alert the user the method steps that are occurring. The automated method may include the following fault states, which cause the system 10 to abort the method: failure to achieve final terminal pressure in a defined time period (vacuum pump fault), overly high ambient temperature, very low ambient temperature, and manual interruption of the sterilization cycle by a user pressing the "STOP" actuator. In the event of a fault condition, the atmospheric air solenoid is opened the re-pressurize the chamber, and the user is instructed to take appropriate action to correct the fault condition.

Another method of sterilizing the materials using the systems 10, 10' is as follows. The materials are introduced into the vessel 14, the lid 18 is installed, and the vacuum source 104 actuated (e.g., the vacuum source 104 is turned on or a valve 212c is opened). Once the chamber 22 has reached a vacuum level below the room-temperature vapor pressure of hydrogen peroxide (e.g., 5 mm Hg at 30 degrees Celsius), a pre-determined amount of the hydrogen peroxide solution 12 is automatically dispensed into the vessel 14 via the dispenser 232 (e.g., a dip tube) until all the solution is evaporated. That is, evaporation under the low-pressure conditions should continue until a partial pressure of hydrogen peroxide vapor reaches a first-predetermined level (e.g., is 5 mm Hg at 30 degrees Celsius) and a partial pressure of water vapor reaches a second pre-determined level (e.g., is 31 mm Hg at 30 degrees Celsius). The first sterilization cycle then occurs for a first predetermined treatment time (e.g., exposure time). Again, one or more sterilization cycles may occur depending on the materials being sterilized. The re-evacuation step is then performed in which the vacuum source 104 is then re-actuated and hydrogen peroxide vapor and water vapor evacuated from the vessel 14. The vessel 14 is then re-pressurized using atmospheric air (via the valve 212a) and the sterilized materials removed from the vessel 14. In some constructions, the re-evacuation step may be omitted if there is a desire to cause the liquid water and hydrogen peroxide to condense onto the surfaces of the materials as air is reintroduced.

With specific reference to FIG. 9, in addition to pulling, by the vacuum source 104, vacuum on an entirely dry system, the method further includes dispensing hydrogen peroxide solution 12 into the sterilization chamber 22 of the vessel 14 with the vacuum source 104 and purge tank 204, if used, being isolated. That is, the second and third valves 212b, 212c are closed in FIG. 9. The method further includes opening the purge tank 204, via opening the second valve 212b, to reduce water vapor. That is, water vapor is drained into the container 224. The method further includes evaporating the hydrogen peroxide in the hydrogen peroxide solution 12 to sterilize the materials positioned within the vessel 14. That is, the second and third valves 212a are open to evaporate the hydrogen peroxide in the hydrogen peroxide solution 12. The method further includes re-introducing, by opening the first valve 212a, to the dry the chamber 22 of the vessel 14.

Regardless of the method used, after treatment is complete, relevant disposal guidelines should be followed to ensure safe and environmentally conscientious treatment of waste products generated by the system. The receptacle 38 with the nonreactive fiber matrix 34 and hydrogen peroxide solution 12 in it is removed from the chamber 22. The nonreactive fiber matrix 34 is removed from the receptacle 38 and disposed of in a hydrogen peroxide-compatible chemical solid waste collection process. Any remaining hydrogen peroxide solution 12 is disposed of in a peroxide-compatible chemical liquid waste collection process. The receptacle 38 is rinsed with water and left to air-dry. The receptacle 38 may be reused in subsequent treatment cycles. After every 30 treatment cycles, vacuum pump oil should be replaced with automotive vacuum pump oil to maintain pump performance.

The disclosed systems 10, 10' improve upon existing vaporized hydrogen peroxide treatment processes by increasing the rate at which hydrogen peroxide solution 12 can be vaporized without the need for active aerosolization or vaporization. The use of nonreactive materials in the nonreactive fiber matrix 34 also reduces the waste consumption of hydrogen peroxide as the solution is vaporized, and simultaneously avoids the risk of explosive or violent decomposition of hydrogen peroxide that may become concentrated as the solution evaporates. The treatment process is also optimized for use in applications where space is limited or the installation of larger dedicated vacuum chambers is prohibitively costly. Also, importantly, the vessels 14 and other components of the systems 10, 10' are easy to move, relatively inexpensive, and can be installed in large quantities as needed.

The disclosed systems 10, 10' may be used in industrial, medical, consumer, or other applications, such as fields where a vaporized hydrogen peroxide treatment process may be utilized. For example, the disclosed systems 10, 10' may be used for the disinfection and sterilization of medical equipment and personal protective equipment and industrial vaporized hydrogen peroxide processing.

Methods

Given the low cost and scalability of the systems 10, 10', the systems 10, 10' were subjected to various experimental tests to demonstrate efficacy for sterilization of surgical N95 respirators based on standards for minimum performance as dictated by the FDA and NIOSH. Validating a system for sterilization of N95s involves not only biological validation but also consideration of the effects of sterilization on standards such as fit, inhalation resistance, and most importantly an N95's required filtration efficiency of 95% or higher for non-oily solid and liquid aerosols. Furthermore, any surgical mask such as a surgical N95 must be validated for fluid-resistant performance as required by the FDA. A sterilization system used by healthcare facilities and certain industries and communities should not allow the performance of N95s to fall below FDA and NIOSH guidelines. Based on these criteria, the system's virucidal capability, impact on the filtration efficiency of N95 respirators, and effect on N95 respirator hydrophobicity were experimentally validated.

Analytical Derivation of Vaporized Hydrogen Peroxide Concentration

The concentration of VHP directly affects the biocidal capabilities of a VHP sterilization system. Thus, the VHP concentration inside the system were both analytically and experimentally determined. Raoult's law was used to determine the partial pressure of VHP in the vacuum chamber as a function of total chamber pressure and concentration of hydrogen peroxide feedstock solution. Raoult's law can be expressed as:

$$p_i = p_1^* * xi$$

where $p_i$ is the vapor pressure of a single compound in a mixture of liquids at a given temperature, $p_1^*$ is the vapor pressure of that compound in its pure form, and xi is the mole fraction of the compound in the solution. If both the vapor pressure at a given temperature of pure hydrogen peroxide and the mole fraction of hydrogen peroxide in the hydrogen peroxide solution are known, the partial pressure of hydrogen peroxide in the gas phase can be calculated. As a result, the concentration in parts per million (ppm) of hydrogen peroxide in the gas phase can be determined if the total pressure of gases in the chamber is known.

The mole fraction of hydrogen peroxide in aqueous solution is found using the equation below:

$$x_1 = \frac{m_i/M_i}{\Sigma_j\ m_j/M_j} = \frac{w_{H2O2}/M_{H2O2}}{w_{H2O2}/M_{H2O2} + w_{H2O}/M_{H2O}}$$

where $W_{H2O2}$ is the mass fraction of hydrogen peroxide in the solution, $W_{H2O}$ is the mass fraction of water in the solution, $M_{H2O2}$ is the molar mass of hydrogen peroxide, and $M_{H2O}$ is the molar mass of water. From the periodic table of the elements, it can be determined that the molar mass of water is 18.02 g/mol and the molar mass of hydrogen peroxide is 34.01 g/mol. For a 3% weight fraction solution of hydrogen peroxide, the mole fraction is found as shown below:

$$x_{H2O2} = \frac{0.03/34.01}{0.03/34.01 + 0.97/18.02} = 0.1612\ \text{mol/mol}$$

In the case of the system 10, 10' described, the vapor pressure of pure hydrogen peroxide at 25° C. is given as 2.1 torr. It can therefore be established that based on Raoult's law, the partial pressure of hydrogen peroxide in a 3% weight fraction solution at 25° C. is 0.03385 torr as shown below:

$$p_{H2O2} = p_{H2O2}^* x_{H2O2} = (2.1\ \text{torr})\left(0.01612 \frac{\text{mol}}{\text{mol}}\right) = 0.03385\ \text{torr}$$

The gas concentration can be expressed as the ratio of the number of particles of the gas of interest to the number of particles of all gases in the container, or equivalently the ratio of the partial pressure of the gas of interest to the total pressure of all gases in the container. This concentration may be expressed in parts per million (ppm) as shown below:

$$PPM_{H2O2} = (p_{H2O2}/P_{chamber}) * 1000000$$

If the target concentration of vaporized hydrogen peroxide is given as 1200 ppm, the absolute pressure of all gases in the vacuum chamber is therefore 28.21 mmHg, as shown below:

$$P_{chamber} = 1000000 * (p_{H2O2}/PPM_{H2O2}) = 100000 * (0.03385 \text{ torr})/(1200 \text{ ppm})$$

$$P_{chamber} = 28.21 \text{ torr} = 28.21 \text{ mmHG}$$

Experimental Validation of Vaporized Hydrogen Peroxide Concentration

Hydrogen peroxide ($H_2O_2$) 50% weight fraction, potassium permanganate (KMnO4), sodium oxalate, and sulfuric acid were purchased from Sigma Aldrich. The solutions were prepared using MilliQ water. High-level peroxide test strips were obtained from Bartovation. All the solutions were kept in light-blocking caramel containers tightly closed in the dark at a temperature between 2 to 8° C. Relative pressure was measured with a digital manometer Dwyer series 475 mark III. The colorimetric absorption change was measured by an Arizona State University-developed iOS application installed on an Apple iPhone 6, which provides high quality imaging hardware and software.

All solutions, including commercially available $H_2O_2$ 3% weight fraction, were titrated by the well-known standard redox method with KMnO4, previously standardized with sodium oxalate. Each solution was acidified with concentrated sulfuric acid.

The same procedure previously described was followed. For all the tests, 40 mL of solution was used in a chamber of 18 L at room temperature. The amount of 40 mL was selected to ensure adequate solution was present in the chamber to prevent total evaporation of solution, but other amounts may be used if it is ensured that the solution does not evaporate completely during system operation. The chamber was closed after 5 minutes of maximum vacuum and treated for 1 hour.

The strips were dipped into MilliQ water for 2 seconds, removed, and shaken to eliminate excess water. Three strips were used per test. A patch was designed with aluminized Mylar film, a gas barrier, to cover the strips inside the chamber attached with double sided tape. After one hour a cord was pulled allowing the exposure of the strips to the vapor for 30 seconds. Before re-introducing air in the chamber, the Relative Pressure ($P_{rel}$) was measured. The pictures were taken immediately after opening the chamber. The iOS application allows three pictures per strip, having as reference a strip with no reaction or previous treatment.

The data was obtained from a laboratory-custom apparatus in a comma-separated (csv) file with corresponding red, green, and blue (RGB) intensities for the reference and sensor strip, and absorbance for each component was also provided. The calibration curve was plotted as the difference between the average of the red absorbance for the three strips at the end of the experiment and the corresponding to 0 ppm (MilliQ water). The $H_2O_2$ vapor concentrations ($x_{H2O2,v}$ and $ppm_v$ concentration) were calculated by Dalton's Law considering the chamber's absolute total pressure (calculated from a measured differential pressure by a gauge the atmospheric pressure), and the $H_2O_2$ partial pressure, previously calculated from literature data containing information of $H_2O_2$ equilibrium partition and the liquid $H_2O_2$ molar fraction (xH2O2, 1) calculated from the molarity determinate by titration.

After each trial, the chamber was washed with water and allowed to dry and ventilate in a fume hood for 20 min.

Validation of virucidal activity using P22 bacteriophages as a proxy for SARS-CoV-2 Viral Preparation and Assay Bacteriophage P22 (ATCC® 19585-B1™) was propagated using *Salmonella typhimurium* (ATCC® 19585™) as the host bacterium using the double agar layer (DAL) technique. Briefly, 1 mL of the sample and 1 mL of the host cell bacteria, in the log-phase of growth, were added to a 5 mL of melted top agar in a test tube which was kept in a water bath at 48 degrees C. The mixture was gently poured onto a bottom agar plate and kept undisturbed to let the top agar to solidify. Then, the plate was incubated upside down at 37 degrees C., and plaques were counted after 24 hours of incubation. A positive and a negative control was included in every DAL assay.

The bottom agar plates were prepared using Tryptic Soy Agar (TSA) (Difco Laboratories, Division of Becton Dickinson & Co.). Prepared TSA was sterilized using an autoclave, cooled to 55° C. and then dispensed into petri plates (20 ml per plate). TSA in plates were allowed to solidify and then stored at 4 degrees C. until used.

The top agar was prepared using Tryptic Soy Broth (TSB) (Difco) by adding 0.7% agar (Difco). Five mL of the top agar medium were dispensed to test tubes, capped and then autoclaved. The top agar tubes were stored at 4 degrees C. until used.

Inoculation and Test Procedure

A surgical 3M 1860 N95 mask was cut to 2.5×2.5 cm pieces using a sterilized pair of scissors to obtain test coupons. Three coupons were placed in a sterilized petri dish, and each was inoculated with P22 bacteriophages at a total concentration of $1.6 \times 10^8$ PFUs per coupon by transferring 100 µL of the stock solution to their inner surface. The inner surface of the mask was selected based on its higher absorbance capability compared to the outer surface which is highly hydrophobic (data not shown). The inoculated coupons were allowed to dry at room temperature for 5 minutes to equilibrate with the mask material.

Triplicate sets of inoculated coupons were placed in the VHP sterilization system 10 and were operated according to the parameters specified earlier.

After the operation cycle completed, test coupons were retrieved from the system 10. Each coupon was placed in a 50 mL tube containing 30 mL of elution buffer. The tube was vortexed to recover viruses from the coupon, and then the recovered buffer was analyzed using DAL technique.

Validation of N95 Respirator Filtration Efficiency Before and after Treatment

The capture efficiency tests were performed using a custom set-up. Challenge aerosols were generated using a medical nebulizer (drive medical, Port Washington, NY, USA) from aqueous solutions. Tests were performed using fumed silica nanoparticle slurry solutions which have been extensively characterized. The nebulization resulted in a broad challenge aerosol distribution and typical observational range was from 50-200 nm, a range which incorporates particles smaller than individual virions. This challenge aerosol covers the range of aerosols used in the NIOSH tests methods, 75±20 nm NaCl particles for N type masks and dioctyl phthalate (185±20 nm) particles for P99 masks.

The challenge aerosol was passed through a trap bottle to remove larger particles. The aerosol then was measured directly or passed through a 25 mm diameter punch sample of the mask material, held in a filter cassette. The size resolved particle number concentration were determined with a Scanning Mobility Particle Sizer (SMPS) set-up consisting of a TSI 3088 Soft X-Ray neutralizer, a TSI 3082 aerosol classifier, a TSI 3085A Nano differential mobility analyzer (DMA) and a TSI 3752 high concentration condensation particle counter (CPC) (TSI, Shoreview, Minn., USA). All tests were run in triplicate and for at least 10 minutes each. The respirators used for validation were surgical 3M 1860 N95s.

Validation of N95 Respirator Fluid Resistance Before and after Treatment

The fluid resistance of the N95 mask surface of control-group (untreated) and experimental-group (5 cycles of VHP treatment) N95 masks was quantified by means of a water drop deflection test. Distilled water was dropped from a fixed height of 17 cm above the base of the mask onto the surface of a mask. The mask was tilted such that the nose-clip edge of the mask was elevated 5 cm above the base of the mask in order to ensure successful roll-off of drops from the mask surface. A video camera was then used to record the falling drops of water, and the amount of time taken by the drops to traverse the surface of the mask and reach the bottom of the mask was quantified and compared between the control-group masks and the experimental-group masks. Each mask was tested with three different water drops, and three of each type of mask (control and experimental) were used to provide a total of 18 test results for comparison. In addition to the quantitative observations provided by the video recording, it was also qualitatively noted whether any absorption of the water drops into the mask surface was observable. The respirators used for validation were surgical 3M 1860 N95s.

Results

Figure 15:
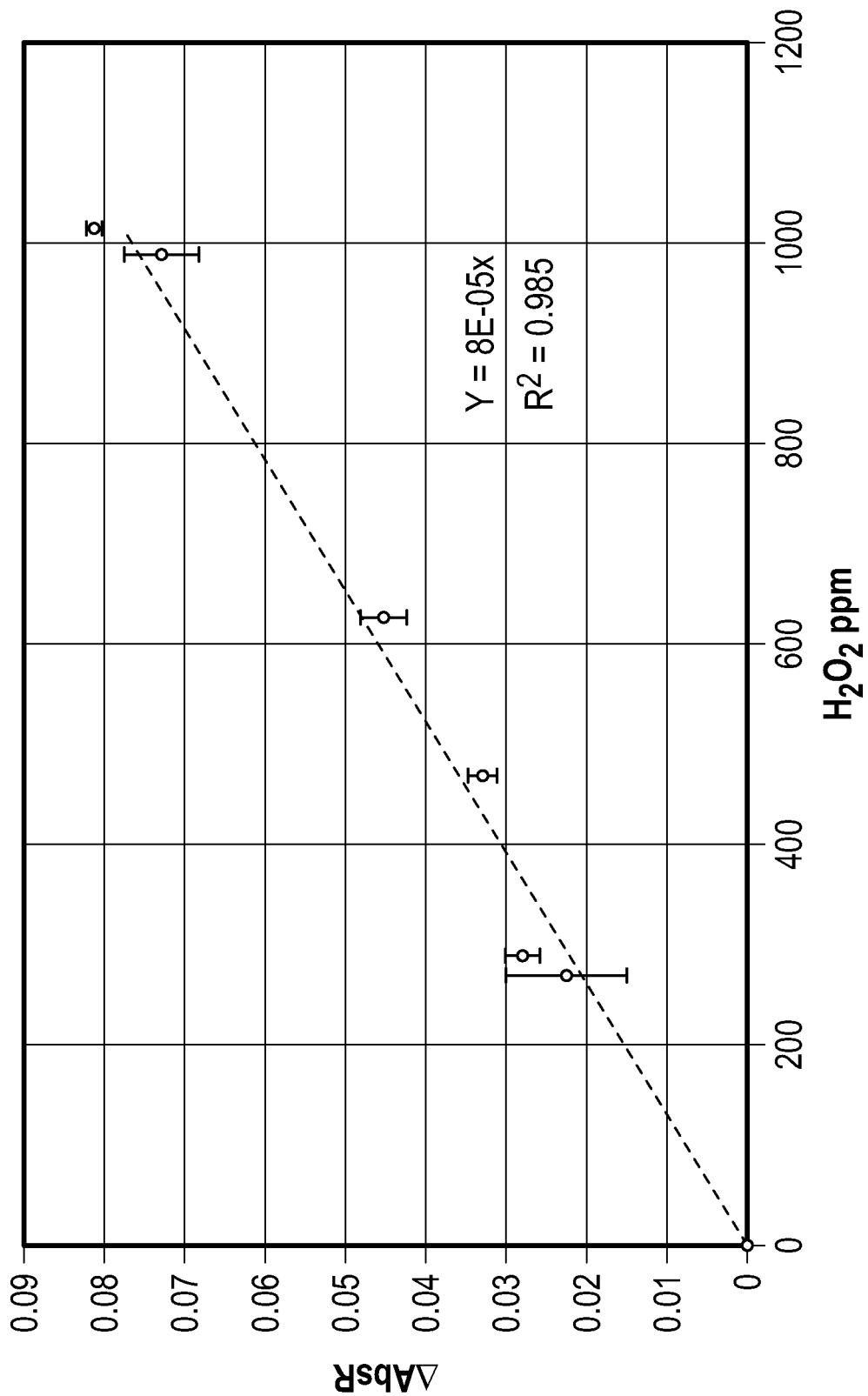
FIG. 15 illustrates a calibration curve for $H_2O_2$ solutions 0-5%.

Experimental Validation of Vaporized Hydrogen Peroxide Concentration in the System A method using commercial peroxide sensor strips with a reaction based on peroxidase and a chromophore compound developing color in the blue-cyan spectrum region was optimized for assessing the concentration of VHP as described in the experimental section. The sensor strips for liquid solutions were adapted and used with the iOS application. Given the reaction chromophore color and comparison with light component absorbance for green, blue and red, we determined the red light component was the most sensitive to use for correlation with the $H_2O_2$ vapor concentration. FIG. 15 shows the calibration curve obtained in the chamber with sensitivity of $8 \times 10^{-5}$ a.u./ppm and an R-squared correlation coefficient (R2) of 0.985. Given this high sensor performance correlation, we were able to determine the $H_2O_2$ vapor concentration under normal system operation conditions for the chamber using a 3% weight fraction $H_2O_2$ solution, which was previously titrated and measured by duplicate as shown in Table 2. This solution provided an operational vapor $H_2O_2$ concentration of 573±107 (SD) ppm. The error bars in FIG. 15 represent the standard deviation of the red light component absorbance.

TABLE 2

Results from experiments run for commercially available $H_2O_2$ 3% weight fraction solution.

| | $P_{rel}^a$ | $P_{atm}^a$ | $P_{Abs}^b$ | $X_{H2O2}$ | Pp | ppm | AbsR$^c$ | ΔAbsR | $C_{H2O2, v}$(ppm) |
|---|---|---|---|---|---|---|---|---|---|
| Test 1 | −0.935 | 1.014 | 60 | 0.0167 | 0.035 | 582 | 0.047802 | 0.037256 | 466 |
| Test 2 | −0.929 | 1.0098 | 60.6 | 0.0167 | 0.0349 | 576 | 0.054483 | 0.043937 | 681 |

In Table 2, P is in bar units, $^b$P is in torr units, and $^c$is the average of the AbsR (a.u.).

Validation of virucidal activity using P22 bacteriophages as a surrogate for SARS-CoV-2

The viral inactivation data is presented in Table 3. The vaporized hydrogen peroxide system achieved sterilization of viruses on N95 mask coupons. In all tests, greater than 6-$\log_{10}$ reductions of P22 bacteriophage were achieved under the test conditions, which surpasses requirements for sterilization. In this experiment, the test samples were exposed to the equilibrium VHP atmosphere within the chamber for a total time of 60 minutes. The observed 6-$\log_{10}$ reduction of the viral proxy (which was a similar result to Yale University's validation of the BQ-50 VHP system (Bioquell, Horsham, PA) and NIOSH and CDC's evaluation of UVGI for sterilization of N95s) demonstrates the system's effectiveness against SARS-CoV-2.

TABLE 3

Inactivation of P22 bacteriophages on
N95 mask coupon using VHP sterilization

| Treatment | Replicate | Initial $\log_{10}$ Inoculated | Initial $\log_{10}$ Recovered | Initial $\log_{10}$ Reduction |
|---|---|---|---|---|
| Vaporized Hydrogen Peroxide | 1 | 8.2 | 1.48 | 6.73 |
| | 2 | 8.2 | 1.78 | 6.45 |
| | 3 | 8.2 | 1.47 | 6.73 |

Validation of N95 Respirator Filtration Efficiency Before and after Treatment

Figure 16:
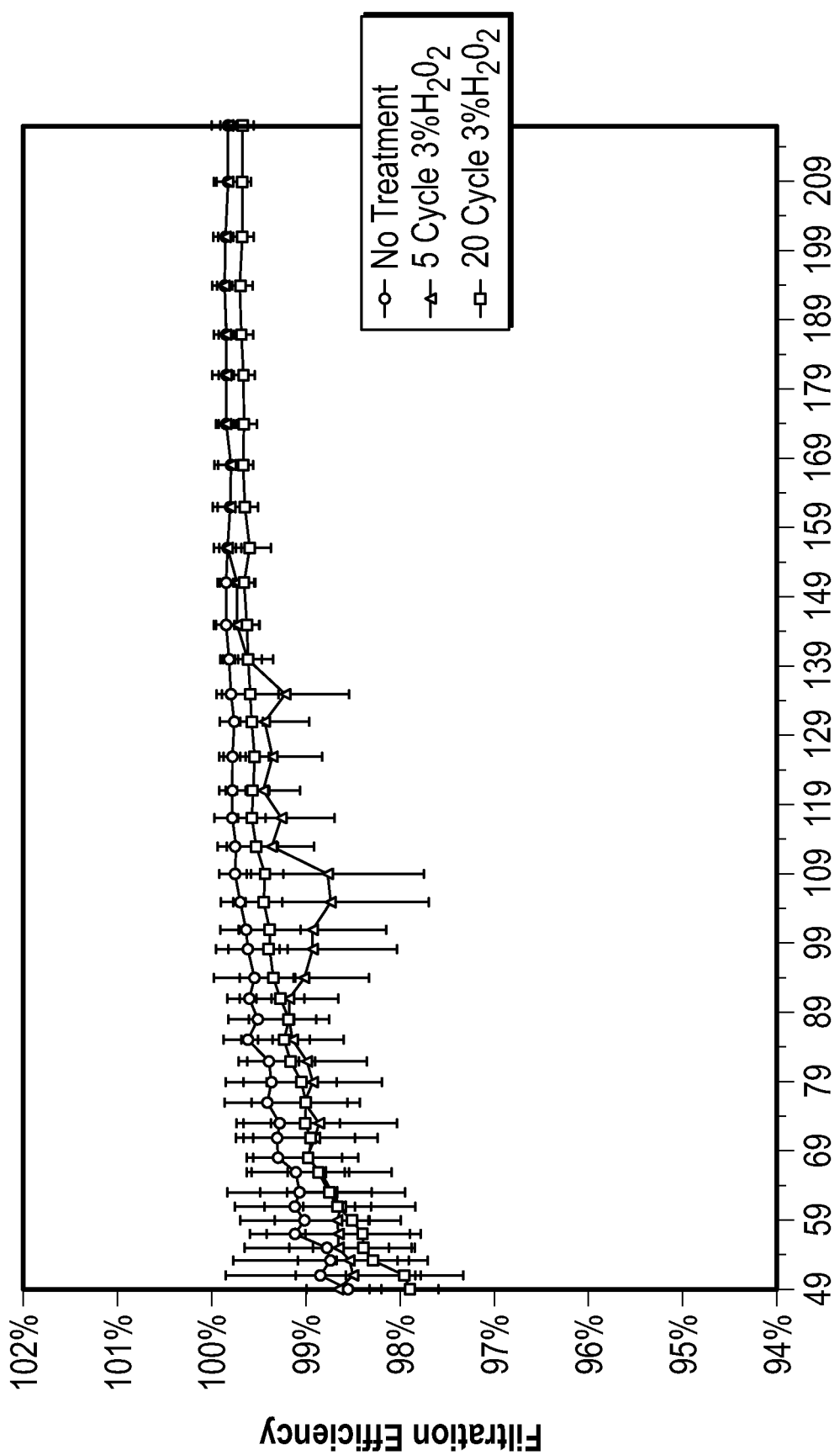
FIG. 16 illustrates a filtration efficiency of untreated N95 respirators, N95 respirators treated with 5 cycles, and N95 respirators treated with 20 cycles with particle challenge sizes from 50 nm to 300 nm.

The filtration validation study conducted as described in the methods section was performed on three new, untreated N95 respirators and on three N95 respirators treated 20 times using the described VHP treatment process. The results of filtration efficiency (as shown in FIG. 16) indicated that at all filtration challenge sizes tested, the measured filtration efficiency of the respirators treated with 20 VHP cycles under the procedures recommended herein remained above the minimum filtration efficiency value of 95% required for the respirators to be classified as an N95 type. The worst-case value of measured filtration efficiency for a 20-cycle treated N95 respirator was found to be 97.89%. These results indicate that the minimum filtration efficiency required for N95 respirator classification is likely to be preserved even beyond 20 treatment cycles.

Validation of N95 Respirator Fluid Resistance Before and after Treatment

The fluid resistance study conducted as described in the methods section yielded the results listed in Table 4. Based on these data, it was shown that the roll-off time increased by an average percent difference of 23% after 5 cycles of VHP treatment. While the ASTM F 1862 standard for testing fluid resistance utilizes synthetic blood at a higher velocity than the droplets used in this non-FDA approved procedure, medical face masks are validated through the FDA by observing that no liquid has penetrated the mask through to the other side. It is notable that no liquid was able to penetrate or absorb through the hydrophobic layer of any of the masks tested.

TABLE 4

Results of a water drop deflection test used to quantify performance of the fluid resistant layer on the N95 respirators before and after 5 cycles of VHP treatment.

| Trial (Experimental) | Roll-Off Time (±17 ms) | Trial (Control) | Roll-Off Time (±17 ms) |
|---|---|---|---|
| Mask 1: Drop 1 | 117 | Mask 4: Drop 1 | 83 |
| Mask 1: Drop 2 | 133 | Mask 4: Drop 2 | 100 |
| Mask 1: Drop 3 | 133 | Mask 4: Drop 3 | 100 |
| Mask 2: Drop 1 | 100 | Mask 5: Drop 1 | 100 |
| Mask 2: Drop 2 | 100 | Mask 5: Drop 2 | 83 |
| Mask 2: Drop 3 | 117 | Mask 5: Drop 3 | 100 |
| Mask 3: Drop 1 | 100 | Mask 6: Drop 1 | 83 |
| Mask 3: Drop 2 | 133 | Mask 6: Drop 2 | 100 |
| Mask 3: Drop 3 | 117 | Mask 6: Drop 3 | 83 |
| Average (ms) | 117 | Average (ms) | 93 |
| Standard Deviation (ms) | 14 | Standard Deviation (ms) | 9 |
| Percent Difference | 23 | | |

DISCUSSION

Common gas-phase disinfectants, such as ethylene oxide (EtO), nitrogen dioxide, peracetic acid, ortho-phthalaldehyde (OPA), glutaraldehyde (Cidex), and ozone, are used to sterilize a variety of healthcare tools and equipment in clinical settings. With the exception of ozone, all of these gases must be obtained as a feedstock material in order to perform sterilization, and many of them possess high toxicity. In particular, ethylene oxide is expensive and known to be carcinogenic and Cidex is an irritant. Furthermore, the required treatment time for EtO is over 12 hours, reducing the throughput of materials through the sterilization system. In contrast, the VHP-based treatment system described in this paper requires only 3% hydrogen peroxide solution, which is inexpensive, widely available, and easy to prepare from higher-concentration solutions if necessary. The byproducts of VHP break down into innocuous water and oxygen, and the treatment cycle requires only 60 minutes in the system described in this paper, with an additional 30-minute aeration phase. Combined, these characteristics make VHP a good disinfectant choice for use in both times of crisis and times of normalcy.

The VHP sterilization systems in common use today are large, high-volume systems that are most suitable to large healthcare facilities where both capital and supporting infrastructure are available. For example, one commonly-employed VHP system is the Bioquell BQ-50 hydrogen peroxide vaporization system. This system is costly, designed to operate in a large dedicated room on the order of 200 cubic meters, and requires a feedstock of 35% hydrogen peroxide solution to operate. Such systems are not well-suited to smaller healthcare sites such as urgent care clinics or assisted living facilities, nor are they accessible to commercial partners or small businesses. The VHP system described in this paper occupies a space less than 1 cubic meter and only requires a standard 3% hydrogen peroxide solution as feedstock. It can also be scaled up to larger installations as needed, simply by using additional units operated in parallel. As such, we believe that the VHP system described in this paper will provide smaller healthcare facilities and other businesses with unprecedented access to easy-to-use, affordable sterilization technology.

To verify the performance of this device, the system's virucidal efficacy, impact on the filtration efficiency of N95 respirators, and compatibility with fluid-resistant N95 respirators were assessed experimentally. In regard to virucidal efficacy, the concentration of VHP in the test chamber was characterized with commercially available hydrogen peroxide test strips under the recommended VHP chamber operating conditions. This test indicated that an operational VHP concentration of 573±107 ppm was achieved in the chamber. This VHP range, 466 ppm-681 ppm, significantly differed from the analytically-derived target concentration of 1200 ppm within the chamber. This disparity can be attributed to several possible causes. In particular, insufficient vacuum level, changes in the surface temperature of the nonreactive fiber matrix (NFM) during vaporization, and potential leaks within the vacuum chamber could have resulted in this disparity.

Despite this difference, the observed reduction in viral load indicates that the process described herein is effective in sterilizing N95 respirators even at the reduced VHP concentrations measured experimentally. In fact, an exposure time of 60 minutes in recommended chamber operating conditions was shown to provide greater than 6-$\log_{10}$ reduction in the P22 bacteriophage used as a surrogate for SARS-CoV-2. This result not only meets but exceeds the ATSM definition for sterilization.

While the sterilization of N95 respirators with a scalable VHP system represents a consequential achievement, the impact would be mitigated if the integrity of the respirator was compromised. However, N95 respirators treated with 20 cycles of 60-minute exposure in the recommended chamber operating conditions remained above the minimum required filtration efficiency of 95% for this type of respirator, indicating that the VHP treatment process does not pose a significant risk to filtration efficiency in the concentrations, time, and number of cycles studied. Similarly, the observed 23% average percent increase in water drop roll-off time after 5 cycles of VHP treatment, combined with the lack of visible liquid penetration, indicates that the recommended VHP conditions did not render the hydrophobic layer unusable. While fit and inhalation resistance testing of the masks before and after treatment were not performed in this study, existing literature suggests that VHP has no detrimental effect on either.

It is important to note that vaporized hydrogen peroxide must be properly destroyed or dispersed before PPE is donned by personnel. NIOSH has established a recommended exposure limit of no greater than 1 ppm time-weighted average for vaporized hydrogen peroxide exposure. Specific guidelines for minimizing exposure of personnel to high hydrogen peroxide levels are addressed in the instructions for use provided with the hydrogen peroxide treatment system. In particular, it is recommended that the operator keep their face away from the VHP treatment chamber during opening and removal of items, and that the VHP treatment chamber be opened in a well-ventilated space. Prior to removing items, the watch glass of hydrogen peroxide solution should be removed from the chamber, the mask loader and items being sterilized should be placed back into the chamber, and the vacuum pump should be run continuously for 30 minutes to evacuate the chamber and remove the remaining VHP from the mask surfaces prior to the removal of masks from the chamber. The system should not be operated if there appears to be any flaw in its construction or visible damage.

As an additional safety precaution, the suggested strength of hydrogen peroxide solution to be used with this system is 3% due to its relatively low concentration. While any solution of hydrogen peroxide can act as an oxidizing agent and should be handled with care as specified by $H_2O_2$'s material safety data sheet, a concentration of 8% or greater of hydrogen peroxide is considered an oxidizer. Using a solution with a concentration of 8% or greater requires more intensive safety measures than outlined in the guidelines for operation of the VHP sterilization systems 10, 10' discussed herein. As an added benefit, 3% hydrogen peroxide solution is also widely available.

Finally, while this work found no significant effect on N95 respirator filtration efficiency after 20 cycles of treatment and only minor effect on fluid resistance of N95s after 5 cycles treatment, consideration must be given to the real world application of a VHP system for N95s. With extended use of N95 respirators during epidemic-related shortages, respirators can experience significant wear and outside debris contamination that limit N95 performance and fit. A decontaminated mask should be inspected before wearing. Sterilized masks should be returned to the original user to prevent adverse effects on fit and performance. Precautions against wear of use on N95 respirators, such as reusing them for less than the validated 20 cycles, should be taken, especially in healthcare settings with extended use of respirators.

CONCLUSION

Achieving a 6-log 10 reduction in P22 bacteriophage viral loads suggests that our VHP system will be effective in eliminating SARS-CoV-2 on N95 respirators. Furthermore, decontaminated N95 respirators showed no significant decrease in standard filtration performance when compared to untreated N95 respirators. Along with existing literature supporting VHP's ability to safely decontaminate N95s, these data demonstrate the capability of this system to effectively sterilize standard N95 respirators and face coverings without a reduction in performance.

While developed and validated for clinical application, the low cost and ease in manufacturing of this system makes it scalable to the needs of businesses operating during the COVID-19 epidemic. The VHP systems 10, 10' described herein can be used by barber shops, schools, and restaurant employees, among a myriad of other applications, to safely sterilize N95 respirators, polypropylene-based masks, and other face coverings for reuse. In addition to respirators, this system may also be suitable for use on hard materials typically found in household and commercial settings, such as tools, office supplies, and other frequently-handled items.

Allowing businesses to safely reuse face coverings and other PPE will have numerous economic and societal benefits. First, this technology will encourage businesses to follow public health guidelines by reducing the financial burden of compliance. While the cost of masks and PPE may seem small, they quickly become significant if each employee is provided with a new face covering daily. However, reusing these coverings will make PPE purchases more infrequent and feasible. This will quickly offset the costs of the sterilization device and can even allow businesses to invest in higher quality PPE when it becomes available.

Helping businesses reuse PPE will also have the added benefit of decreasing overall demand for these devices. This will mitigate the strain on existing PPE supply chains even as increasingly large sectors of the economy resume in-person operations. As a result, this will help ensure that basic PPE remains available throughout the future progression of the COVID-19 pandemic.

Furthermore, incorrect reuse of contaminated facial coverings can decrease efficacy and even act as a vector for viral transmission. Implementation of these VHP treatment systems will give business owners access to technologies never before implemented outside of medical facilities, allowing them to process PPE in the same way it would be treated in a healthcare setting. Thus, business owners can implement re-use of facial coverings with confidence, knowing they are protecting the health of their community as they resume operations.

Finally, the implementation of sterilization devices will inspire consumer confidence as communities resume in-person economic activity. This will be facilitated by the widespread availability of safe, quality facial coverings and PPE to business owners, their employees, and their customers. In turn, consumers will feel safer in these places of business, and will therefore more regularly support businesses, bolstering the newly reopened economy. Taken together, this work highlights the efficacy of the novel, scalable, and cost-effective VHP system, which can be rapidly deployed for both clinical and community applications.

Various features and advantages of the invention are set forth in the following claims.

What is claimed is:

1. A sterilization system comprising:
   a vessel defining a chamber, the chamber configured to receive one or more materials;
   a hydrogen peroxide solution positioned within the chamber;
   a non-reactive fiber matrix positioned within the chamber;
   a support assembly positioned within the chamber, the support assembly configured to support the one or more materials; and
   a vacuum source in fluid communication with the chamber, the vacuum source configured to evacuate the chamber,
   wherein evacuation of the chamber causes vaporization of the hydrogen peroxide in the hydrogen peroxide solution to disinfect the one or more materials positioned in the chamber,
   wherein the non-reactive fiber matrix is formed of a material that has high surface area, wicking capability, and low reactivity to hydrogen peroxide,
   wherein the non-reactive fiber matrix is positioned within a receptacle formed at a bottom of the chamber, and
   wherein the non-reactive fiber matrix is configured to increase the rate of vaporization of the hydrogen peroxide solution.

2. The sterilization system of claim 1, further comprising a controller and one or more sensors in communication with the controller, the controller configured to control the vacuum source based on feedback from the one or more sensors.

3. The sterilization system of claim 1, wherein the non-reactive fiber matrix includes a woven fiberglass mat, or a nonwoven fiberglass mat.

4. A sterilization system comprising:
- a vessel defining a chamber configured to receive one or more materials;
- a purge tank fluidly connected to the vessel via a first conduit
- a first valve positioned within the first conduit, wherein the purge tank is configured to capture vapor from the chamber when the first valve is in an open position;
- a hydrogen peroxide solution positioned within the chamber;
- a non-reactive fiber matrix positioned within the chamber;
- a vacuum source fluidly connected to the vessel and the purge tank via a second conduit; and
- a second valve positioned within the second conduit, wherein the vacuum source is configured to evacuate the chamber when the first valve is in the open position and the second valve is in an open position;
- wherein evacuation of the chamber with the vacuum source causes vaporization of the hydrogen peroxide in the hydrogen peroxide solution to disinfect the one or more materials positioned in the chamber,
- wherein the non-reactive fiber matrix is formed of a material that has high surface area, wicking capability, and low reactivity to hydrogen peroxide,
- wherein the non-reactive fiber matrix is positioned within a receptacle formed at a bottom of the chamber, and
- wherein the non-reactive fiber matrix is configured to increase the rate of vaporization of the hydrogen peroxide solution.

5. The sterilization system of claim 4, further comprising a controller and one or more sensors in communication with the controller, the controller configured to control the vacuum source based on feedback from the one or more sensors.

6. The sterilization system of claim 5, wherein the controller is configured to control the first valve and the second valve to control the vacuum source based on feedback from the one or more sensors.

7. The sterilization system of claim 4, wherein the non-reactive fiber matrix includes a woven fiberglass mat, or a nonwoven fiberglass mat.

8. The sterilization system of claim 4, wherein the hydrogen peroxide solution is fed into the chamber with a dispenser, the dispenser being configured to automatically dispense hydrogen peroxide solution into the chamber of the vessel.

9. A method of sterilizing one or more materials, the method comprising:
- providing a sterilization system of claim 1;
- positioning the one or more materials within the chamber;
- combining the hydrogen peroxide solution with the non-reactive fiber matrix within the vessel; and
- vaporizing the hydrogen peroxide in the hydrogen peroxide solution to sterilize the one or more materials within the chamber.

10. The method of claim 9, wherein the vaporizing the hydrogen peroxide in the hydrogen peroxide solution includes evacuating, with the vacuum source, the chamber.

11. The method of claim 9, further comprising actuating the vacuum source to achieve a vacuum level that is below a room-temperature vapor pressure of hydrogen peroxide.

12. The method of claim 9, wherein the combining the hydrogen peroxide solution with the non-reactive fiber matrix includes dispensing the hydrogen peroxide solution into the chamber until some or all of the hydrogen peroxide solution is evaporated.

13. The method of claim 9, further comprising evaporating the hydrogen peroxide solution under low-pressure conditions.

14. The method of claim 13, further comprising evaporating the hydrogen peroxide solution until a partial pressure of hydrogen peroxide vapor reaches a first pre-determined level and a partial pressure of water vapor reaches a second pre-determined level.

15. The method of claim 14, further comprising actuating the vacuum source and evacuating the hydrogen peroxide vapor and water vapor from the chamber.

* * * * *